United States Patent
Yen et al.

(10) Patent No.: US 9,831,444 B1
(45) Date of Patent: Nov. 28, 2017

(54) PHENANTHROLINE-BASED COMPOUND FOR ORGANIC ELECTROLUMINESCENCE DEVICE

(71) Applicants: Feng-Wen Yen, Taipei (TW); Li-Chieh Chuang, Nantou (TW); Chin-Min Teng, Miaoli (TW)

(72) Inventors: Feng-Wen Yen, Taipei (TW); Li-Chieh Chuang, Nantou (TW); Chin-Min Teng, Miaoli (TW)

( * ) Notice: Subject to any disclaimer, the term of this patent is extended or adjusted under 35 U.S.C. 154(b) by 32 days.

(21) Appl. No.: 15/210,910

(22) Filed: Jul. 15, 2016

(51) Int. Cl.
*H01L 51/50* (2006.01)
*H01L 51/00* (2006.01)
*C09K 11/06* (2006.01)
*C09K 11/02* (2006.01)
*C07F 1/02* (2006.01)
*C07D 471/04* (2006.01)

(52) U.S. Cl.
CPC ........ *H01L 51/0077* (2013.01); *C07D 471/04* (2013.01); *C07F 1/02* (2013.01); *C09K 11/02* (2013.01); *C09K 11/06* (2013.01); *H01L 51/0056* (2013.01); *H01L 51/0067* (2013.01); *H01L 51/0072* (2013.01); *H01L 51/0085* (2013.01); *C09K 2211/1007* (2013.01); *C09K 2211/1029* (2013.01); *C09K 2211/181* (2013.01); *C09K 2211/185* (2013.01); *H01L 51/5012* (2013.01); *H01L 51/5016* (2013.01); *H01L 51/5072* (2013.01); *H01L 51/5096* (2013.01)

(58) Field of Classification Search
None
See application file for complete search history.

(56) References Cited

FOREIGN PATENT DOCUMENTS

| JP | 2008106015 A | 3/2008 | |
| JP | 2008-106015 | * 5/2008 | ............. H01L 52/50 |
| WO | 2014/097711 A1 | 10/2013 | |

\* cited by examiner

*Primary Examiner* — Gregory Clark

(57) ABSTRACT

The present invention discloses a phenanthroline-based compound and an organic EL device employing the compound as phosphorescent light emitting host material of a light emitting layer and/or electron transporting layer material and/or hole blocking layer material and/or a thermally activated delayed fluorescence (TADF) material of a light emitting layer which can display good performance.

21 Claims, 1 Drawing Sheet

| 14 | —— metal electrode |
| 13 | —— electron injection layer |
| 12 | —— electron transport layer |
| 11 | —— hole blocking layer |
| 10 | —— light emitting layer |
| 9 | —— electron blocking layer |
| 8 | —— hole transport layer |
| 7 | —— hole injection layer |
| 6 | —— transparent electrode |

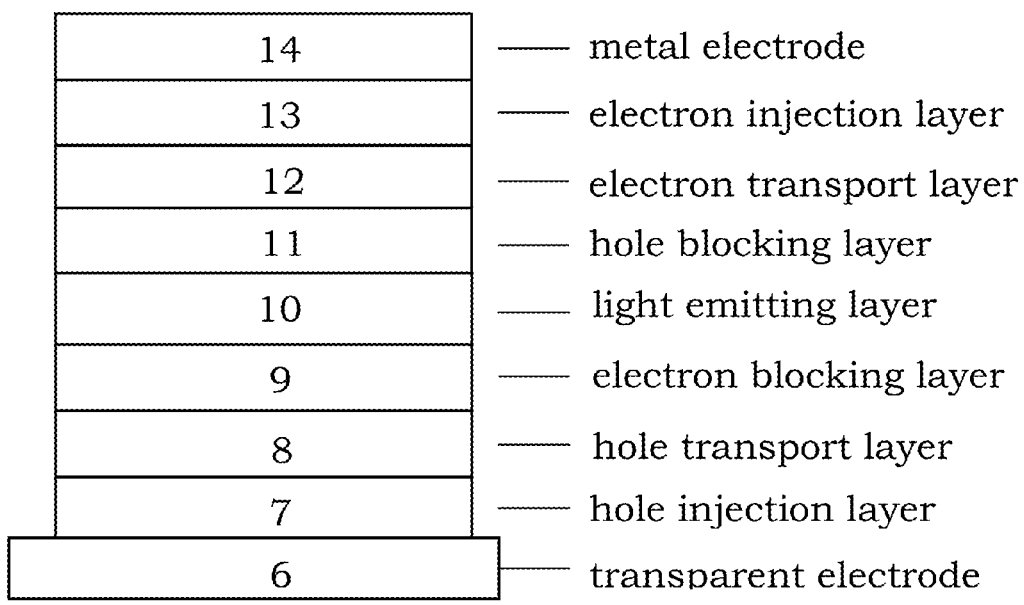

PHENANTHROLINE-BASED COMPOUND FOR ORGANIC ELECTROLUMINESCENCE DEVICE

FIELD OF INVENTION

The present invention generally relates to a phenanthroline-based compound and an organic electroluminescence (herein referred to as organic EL) device using the compound. More specifically, the present invention relates to the compound having general formula (1), and an organic EL device employing the compound as phosphorescent light emitting host material of a light emitting layer and/or electron transporting layer material and/or hole blocking layer material and/or thermally activated delayed fluorescence (TADF) material of a light emitting layer.

BACKGROUND OF THE INVENTION

Organic electroluminescence (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically an organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is finished by some heavy atom such as iridium, rhodium, platinum, palladium and the phosphorescent transition may be observed from an excited MLCT (metal to ligand charge transfer) state of organic metallic complexes.

Recently, a new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the siglet level by the mechanism of reverse intersystem crossing (RISC).

The organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or electron blocking materials must have HOMO (highest occupied molecular orbital) and LUMO (lowest unoccupied molecular orbital) energy levels suitable to block hole or electron transport from the EML to the ETL or the HTL.

For full-colored flat panel displays in AMOLED or OLED lighting panel the material used for the phosphorescent host for emitting layer are still unsatisfactory in half-lifetime, efficiency and driving voltage for industrial practice use. Besides, in order to display excellent performance of organic EL devices, the phosphorescent light emitting host material need to collocate with other organic thin film layer such as hole blocking layer and electron transporting layer to get lower power consumption, longer half-life time and higher efficiency. Therefore, there is a demand for designing and developing novel material for organic EL devices.

SUMMARY OF THE INVENTION

According to the reasons described above, the present invention has the objective of resolving such problems of the prior art and offering a light emitting device which is excellent in its thermal stability, high luminance efficiency and long half-life time. The present invention discloses a phenanthroline-based compound having general formula (1), used as a phosphorescent light emitting host material of light emitting layer, and/or electron transporting layer material, and/or hole blocking layer material, and/or thermally activated delayed fluorescence (TADF) material of a light emitting layer with good charge carrier mobility and excellent operational durability thereby lowering driving voltage and power consumption, increasing efficiency and half-life time of organic EL device.

The present invention has the economic advantages for industrial practice. Accordingly, the present invention discloses a phenanthroline-based compound which can be used for organic EL device. The mentioned phenanthroline-based compound is represented by the following formula (1):

formula (1)

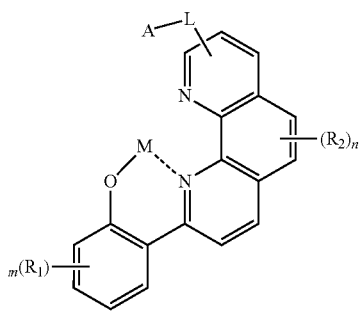

wherein A is selected from the group consisting of formula (2) to formula (8):

formula (2)

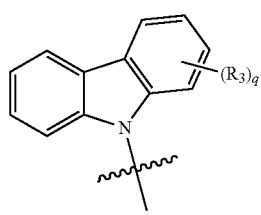

formula (3)

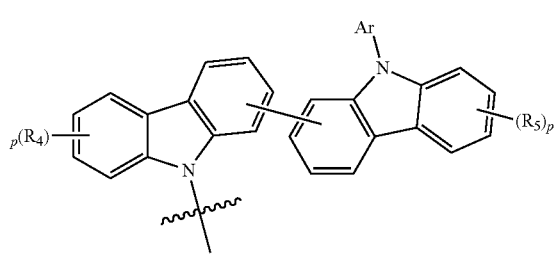

formula (4)

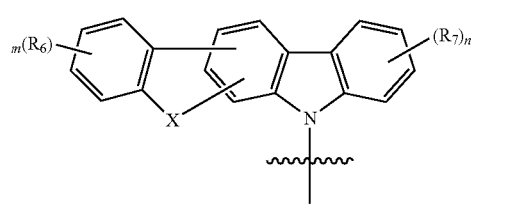

formula (5)

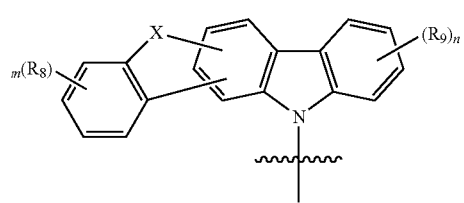

formula (6)

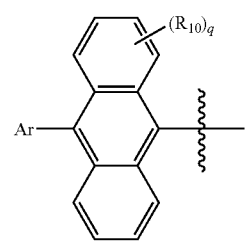

formula (7)

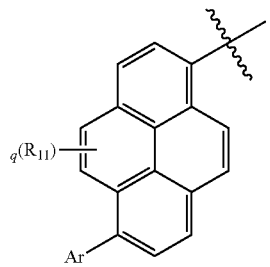

formula (8)

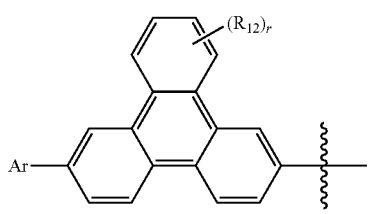

L represents a single bond, a substituted or unsubstituted arylene group having 6 to 30 ring carbon atoms, or a substituted or unsubstituted heterarylene group having 3 to 30 ring carbon atoms, m represent an integer of 0 to 4, n represents an integer of 0 to 6, p represents an integer of 0 to 7, q represents an integer of 0 to 8, r represents an integer of 0 to 10, M represents a metal atom or a non-metal atom; X is a divalent bridge comprising atoms or groups selected from the group consisting of O, S, $C(R_{13})(R_{14})$, $NR_{15}$ and $Si(R_{16})(R_{17})$, Ar is selected from the group consisting of a substituted or unsubstituted aryl group having 6 to 30 carbon atoms or a substituted or unsubstituted heteroaryl group having 3 to 30 carbon atoms, $R_1$ to $R_{17}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

BRIEF DESCRIPTION OF THE DRAWINGS

FIG. 1 shows one example of an organic EL device in the present invention, wherein 6 is transparent electrode, 14 is metal electrode, 7 is hole injection layer which is deposited onto 6, 8 is hole transporting layer which is deposited onto 7, 9 is electron blocking layer which is deposited onto 8, 10 is light emitting layer which is deposited onto 9, 11 is hole blocking layer which is deposited onto 10, 12 is electron transporting layer which is deposited on to 11, and 13 is electron injection layer which is deposited on to 12.

DESCRIPTION OF THE PREFERRED EMBODIMENTS

What is probed into the invention is a phenanthroline-based compound for an organic EL device and the associated device. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, the phenanthroline-based compound which can be used as phosphorescent light emitting host material of a light emitting layer, and/or electron transporting layer material, and/or hole blocking layer material, and/or thermally activated delayed fluorescence (TADF) material of a light emitting layer for an organic EL device is disclosed. The mentioned phenanthroline-based compound is represented by the following formula (1):

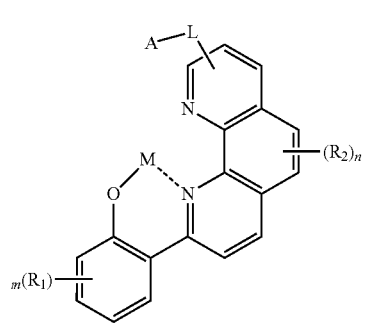

formula (1)

wherein A is selected from the group consisting of formula (2) to formula (8)

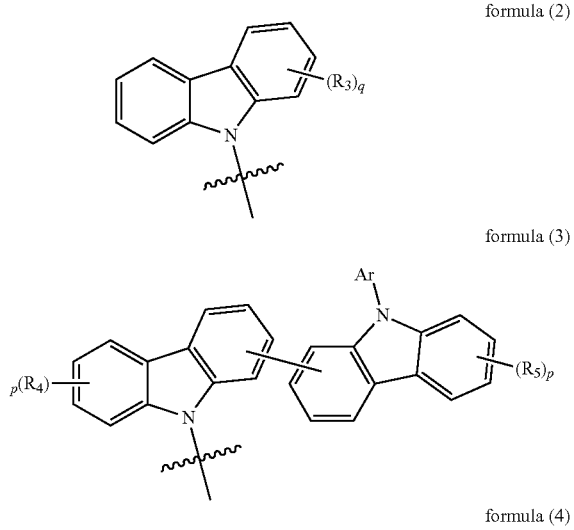

formula (2)

formula (3)

formula (4)

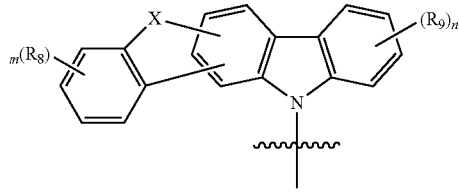

formula (5)

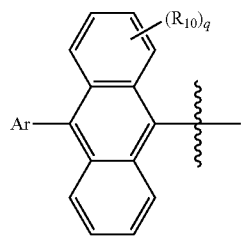

formula (6)

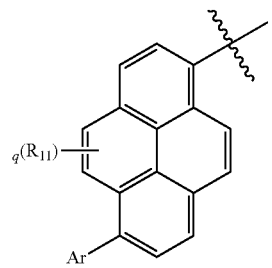

formula (7)

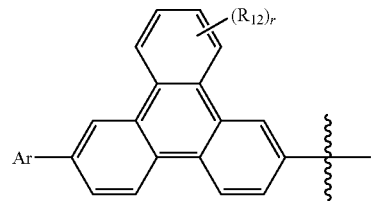

formula (8)

L represents a single bond, a substituted or unsubstituted arylene group having 6 to 30 ring carbon atoms, or a substituted or unsubstituted hetarylene group having 3 to 30 ring carbon atoms, m represent an integer of 0 to 4, n represents an integer of 0 to 6, p represents an integer of 0 to 7, q represents an integer of 0 to 8, r represents an integer of 0 to 10, M represents a metal atom or a non-metal atom; X is a divalent bridge comprising atoms or groups selected from the group consisting of O, S, $C(R_{13})(R_{14})$, $NR_{15}$ and $Si(R_{16})(R_{17})$, Ar is selected from the group consisting of a substituted or unsubstituted aryl group having 6 to 30 carbon atoms and a substituted or unsubstituted heteroaryl group having 3 to 30 carbon atoms, $R_1$ to $R_{17}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

According to the above-mentioned phenanthroline-based compound represented by formula (1), wherein L is represented by the following formula (9):

formula (9)
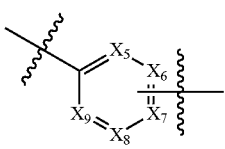
wherein $X_5$ to $X_9$ independently represents a nitrogen atom or $C(R_s)$, and each $R_s$ represents a hydrogen, a halide, a substituted or unsubstituted alkyl group having 1 to 30 carbon atoms, or a substituted or unsubstituted aryl group having 6 to 30 carbon atoms.
In one embodiment, some phenanthroline-based compounds are shown below:
C1
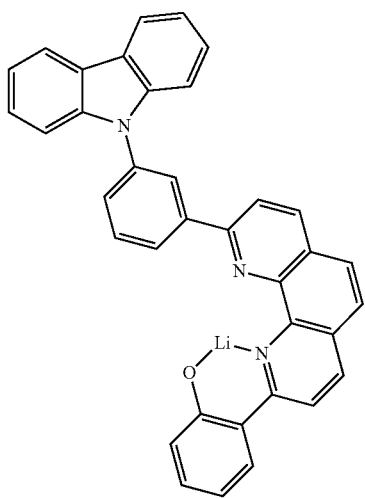
C2
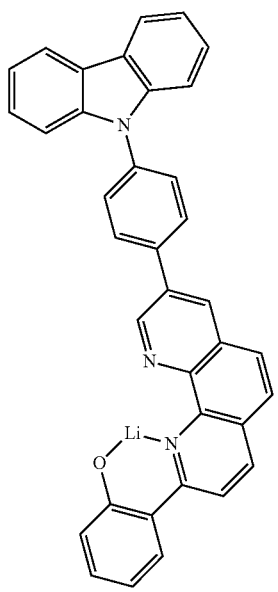
C3
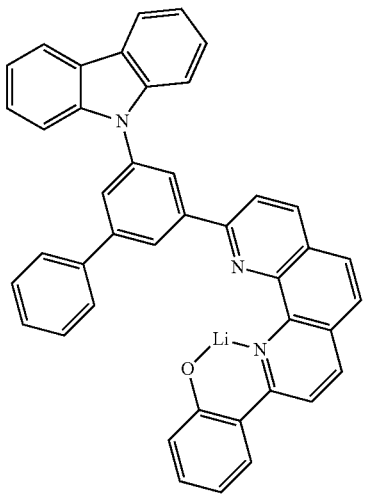
C4
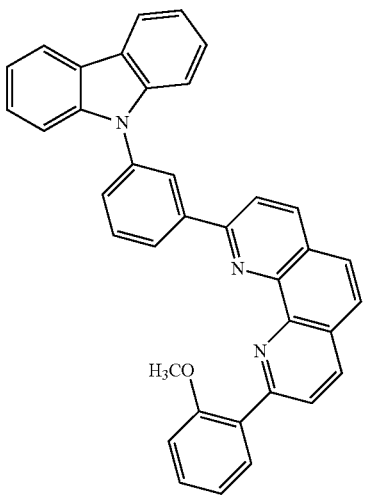
C5
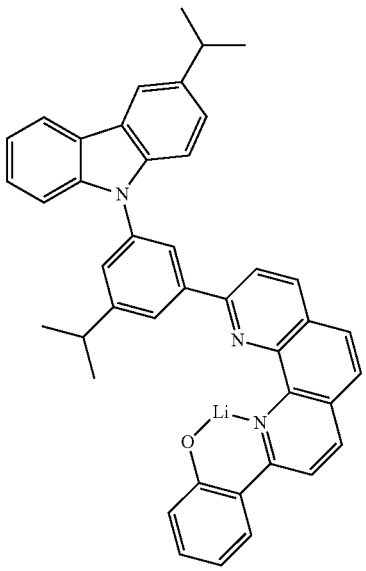

C6
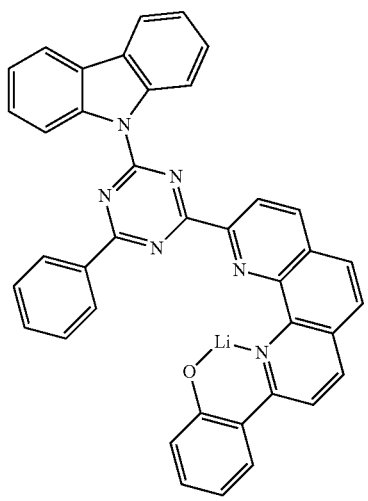
C7
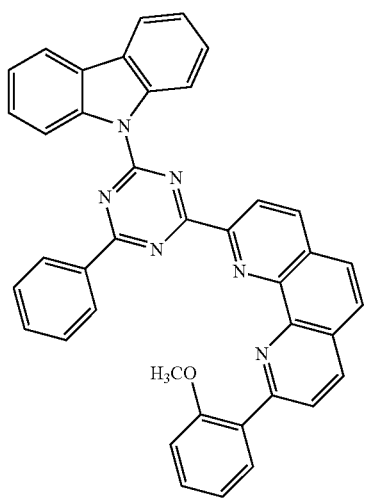
C8
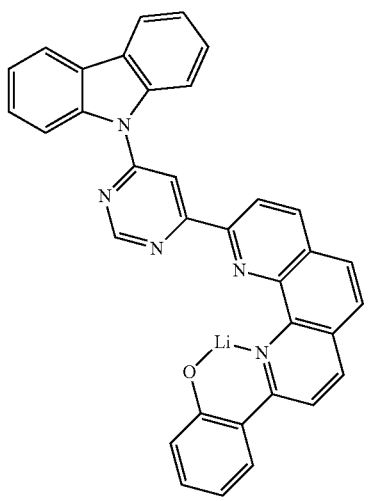
C9
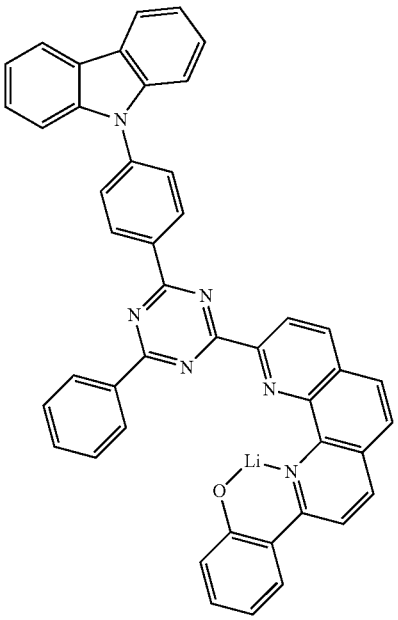
C10
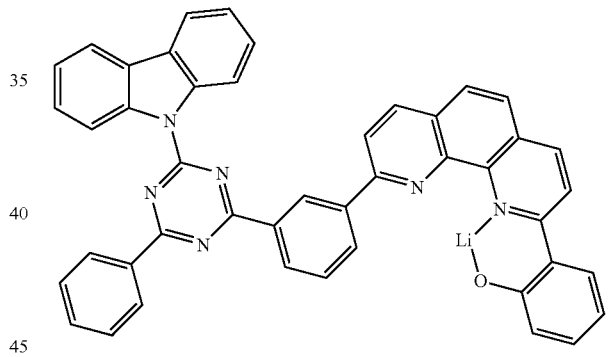
C11
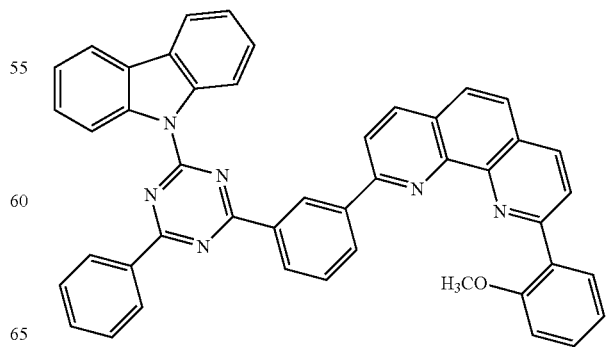

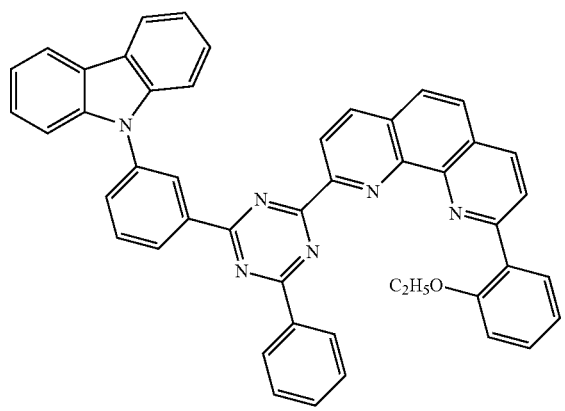
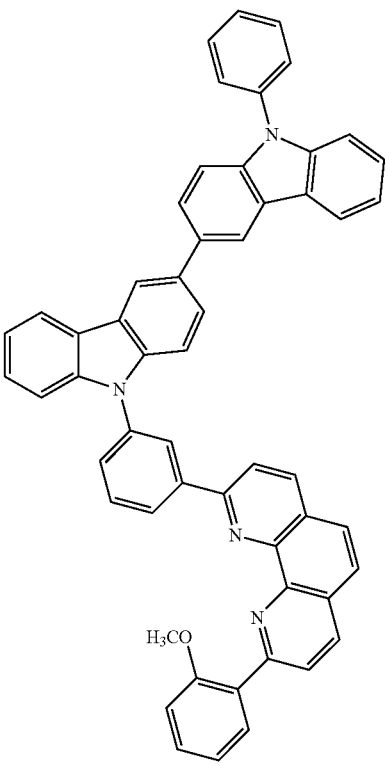
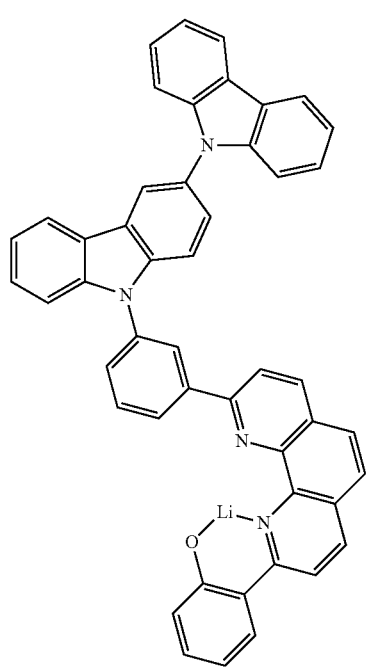
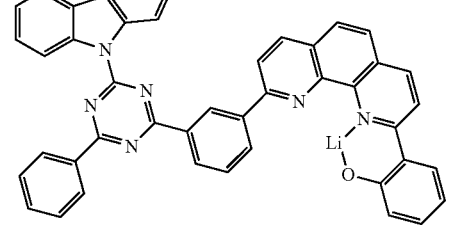

C17
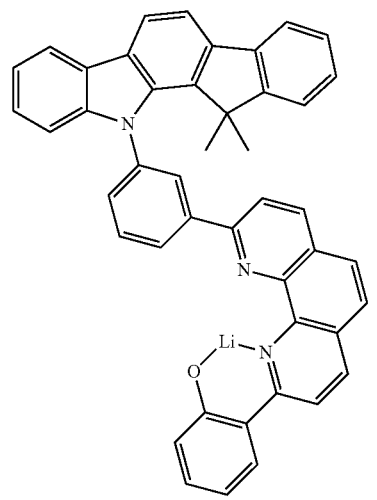
C18
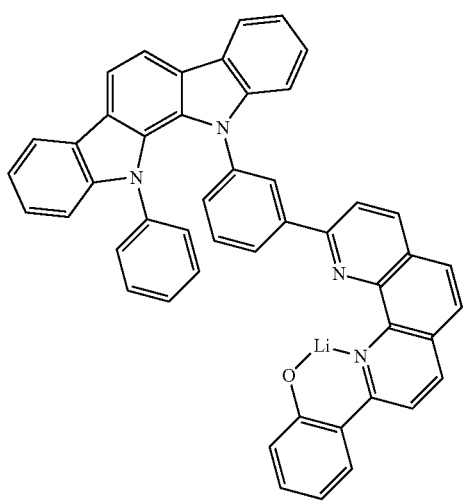
C19
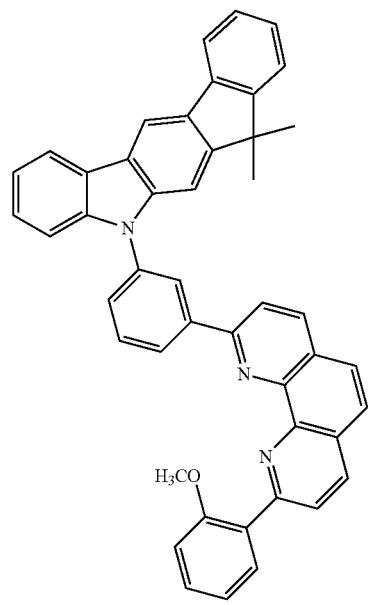
C20
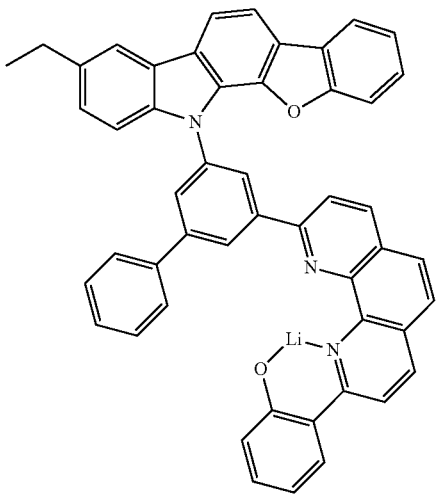
C21
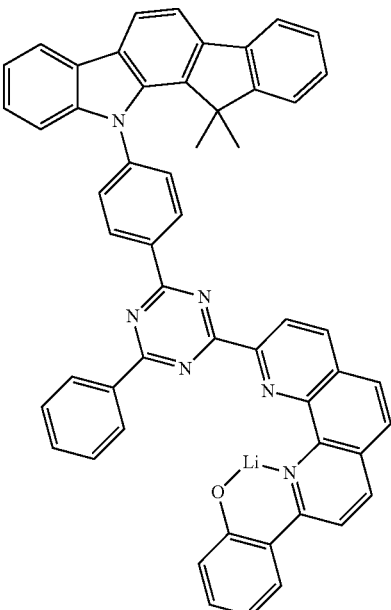
C22
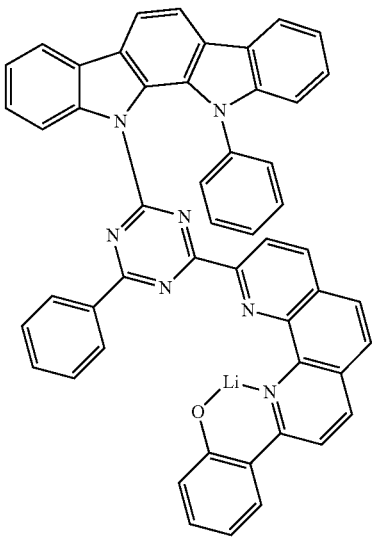

C23
C24
C25
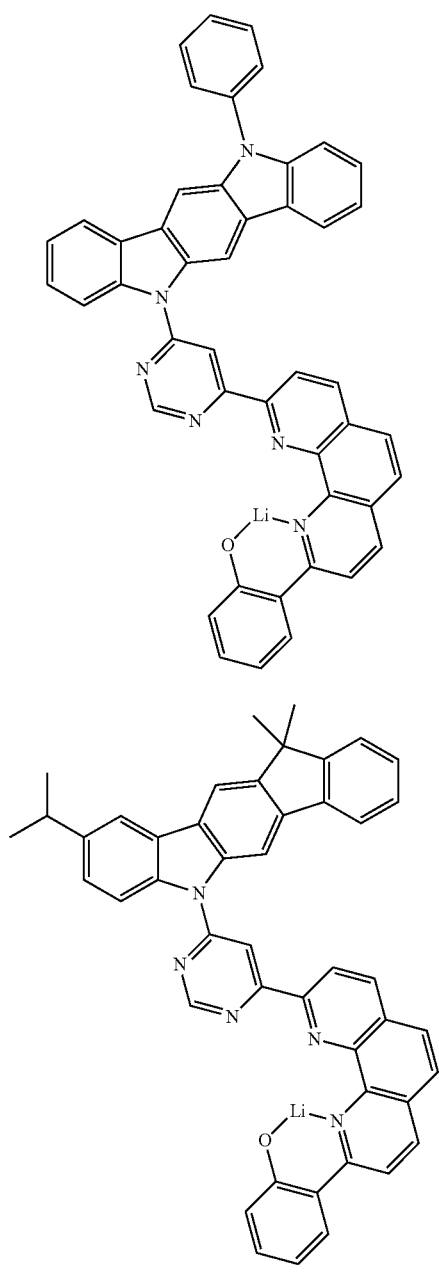
C26
C27
C28
C29
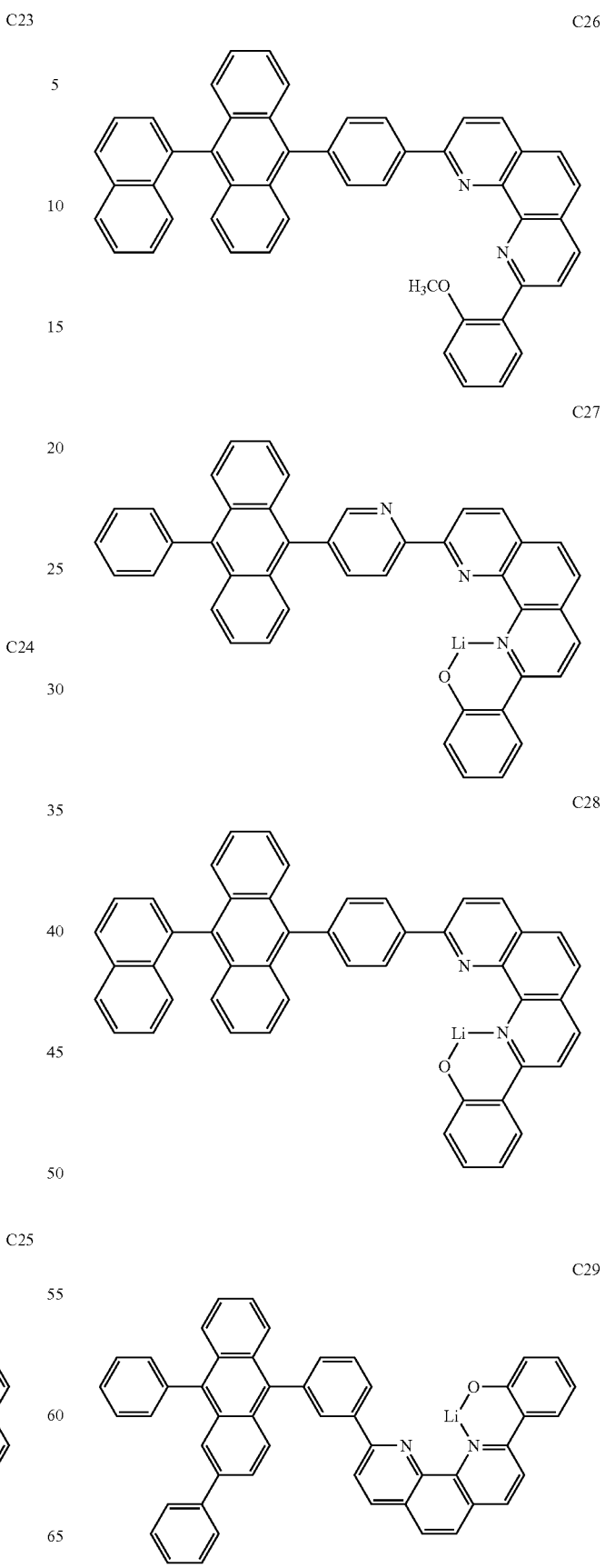

C30
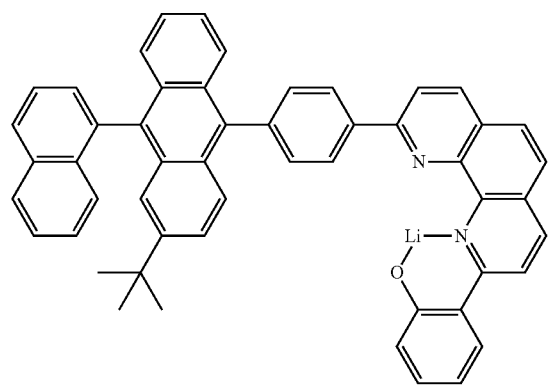
C31
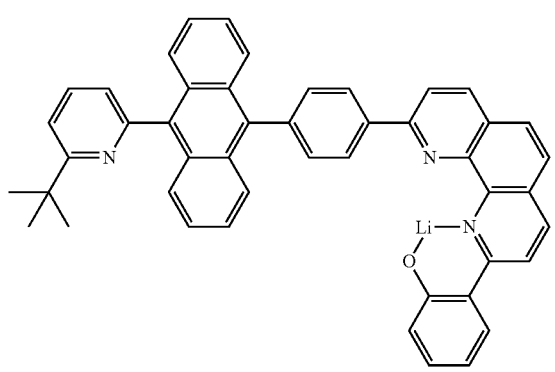
C32
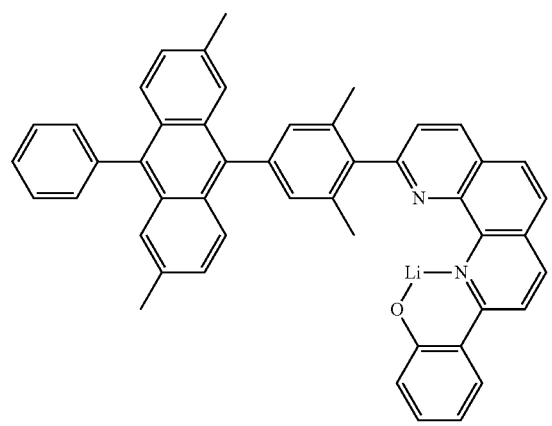
C33
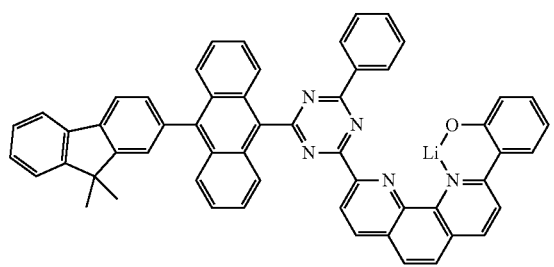
C34
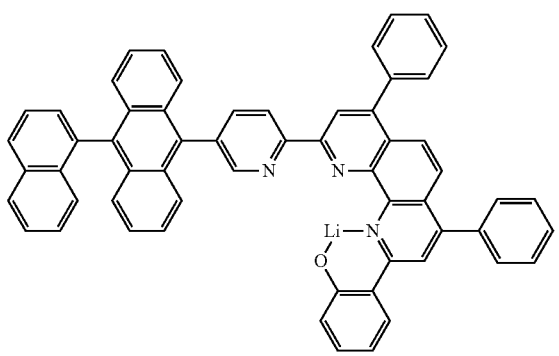
C35
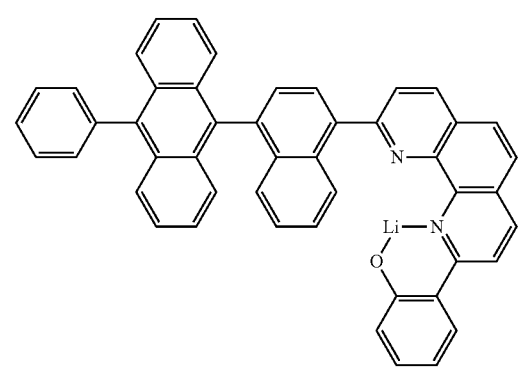
C36
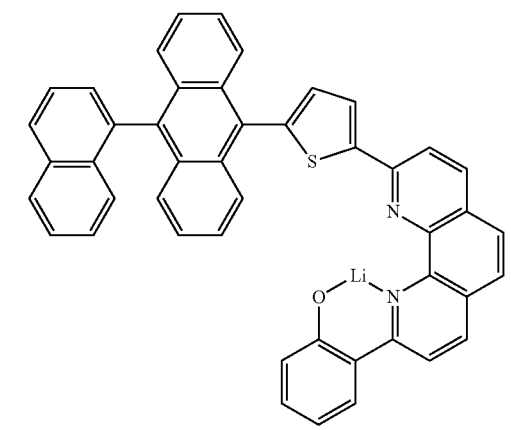
C37
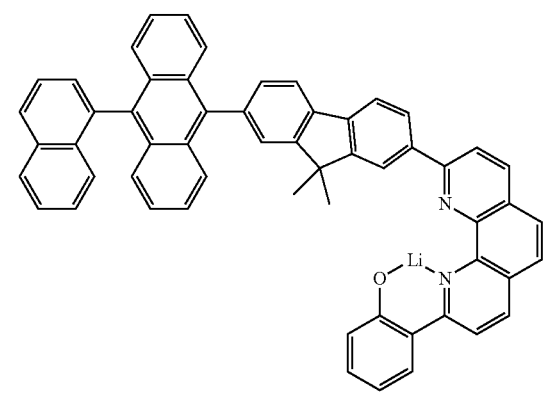

C38
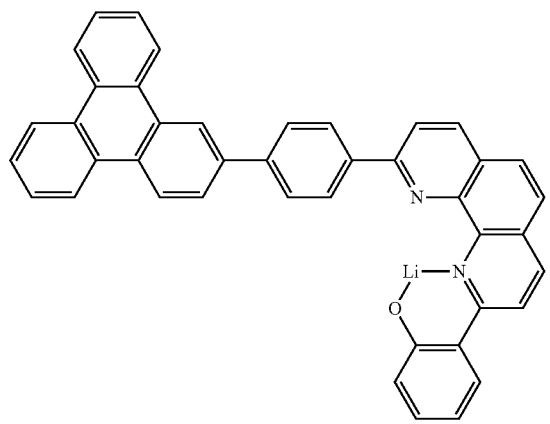
C41
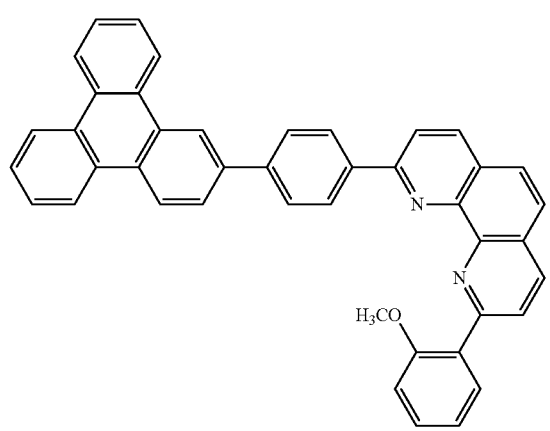
C39
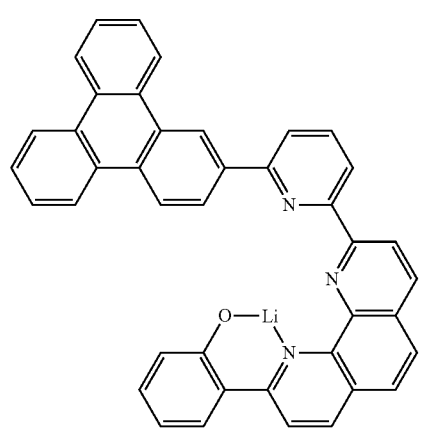
C42
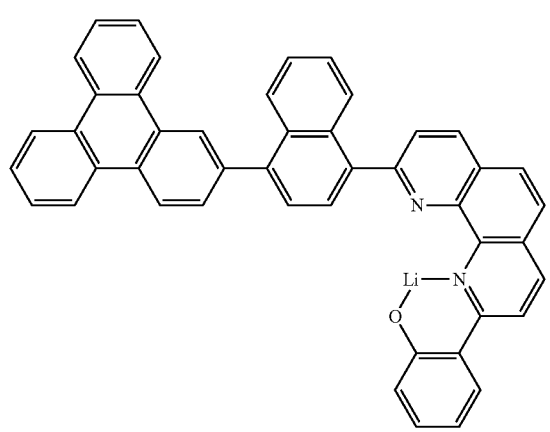
C40
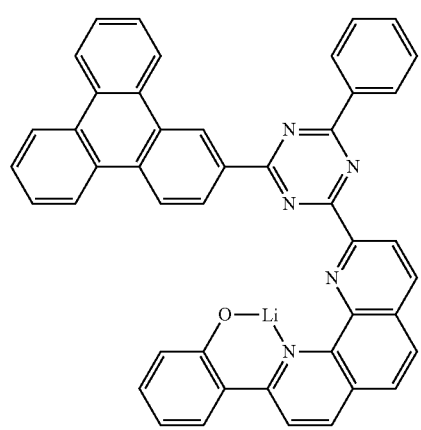
C43
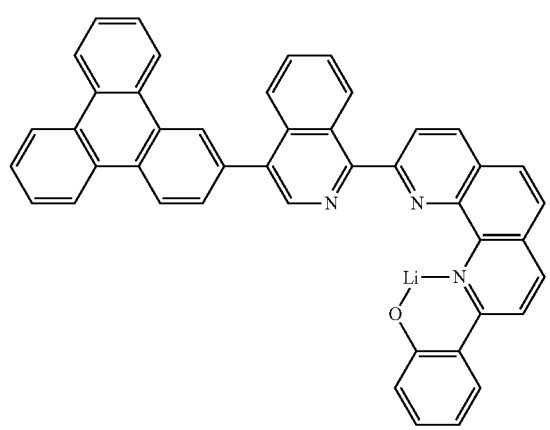

C44
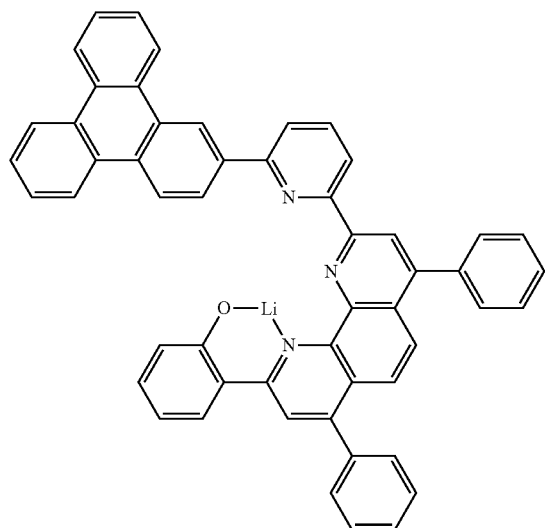
C47
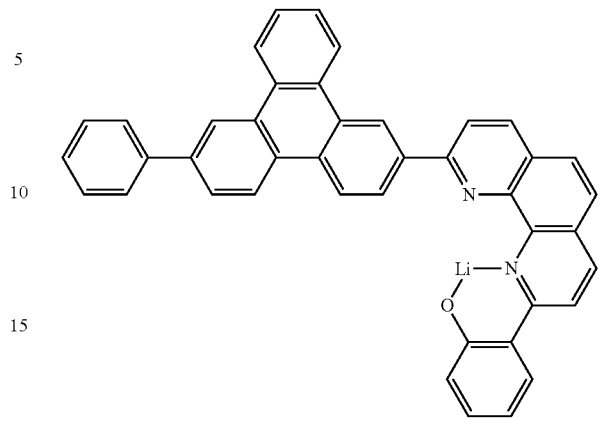
C45
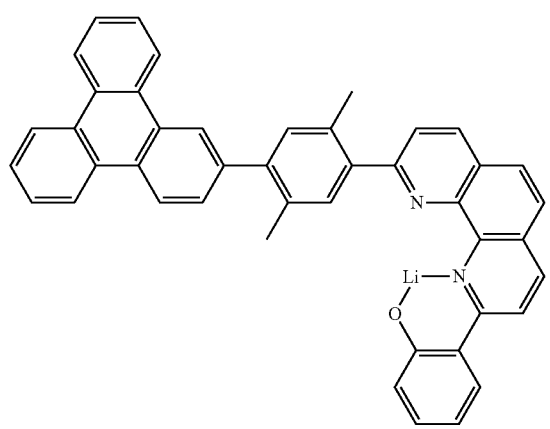
C48
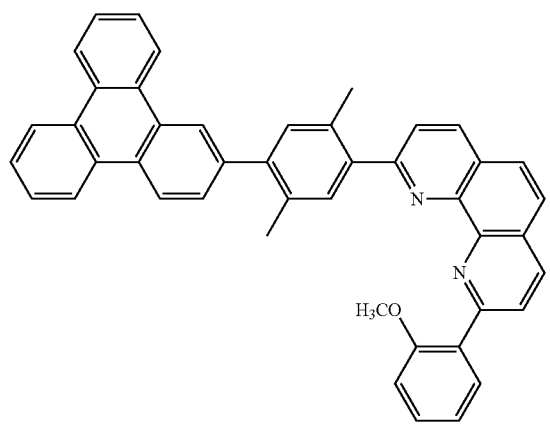
C46
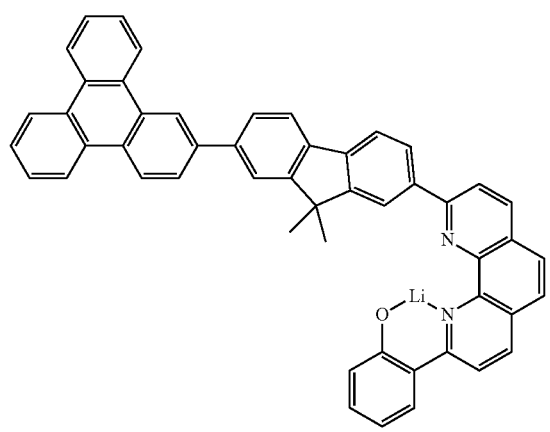
C49
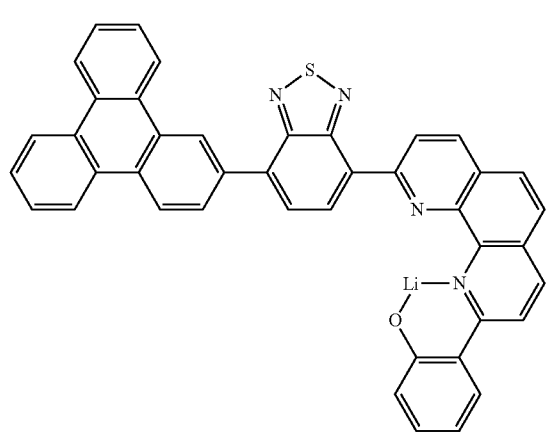

C50

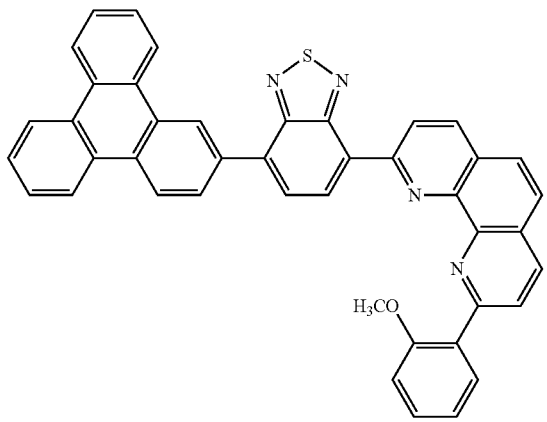

Detailed preparation for the phenanthroline-based compound in the present invention could be clarified by exemplary embodiments, but the present invention is not limited to exemplary embodiments. EXAMPLE 1 to EXAMPLE 9 show the examples for preparation of the phenanthroline-based compound in the present invention. EXAMPLE 10 and 11 show the fabrication of an organic EL device and I-V-B, half-life time testing report of the organic EL device.

Example 1

Synthesis of C1

Synthesis of 2-(2-methoxyphenyl)-1,10-phenanthroline

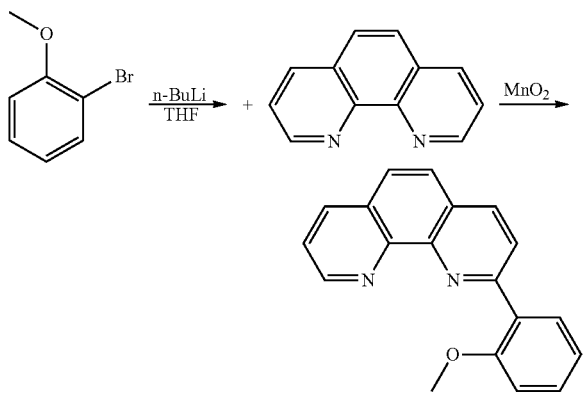

The compound is synthesized by the method provided in Journal of Coordination Chemistry, 62(3), 400-409; 2009. A solution of n-BuLi (107.0 mmol) in hexanes was added to a solution of 2-bromoanisole (20.0 g, 107.0 mmol) in THF (80 mL) under a nitrogen atmosphere at −78° C. The mixture was allowed to warm to room temperature and stirred overnight. The resulting mixture was added dropwise to an ice-cooled solution of 1,10-phenanthroline (9.6 g, 53.5 mmol) in THF (80 mL), and a wine-red solution was obtained. The resulting mixture was refluxed for 12 h, cooled in an ice bath and quenched with water (30 mL). The organic phase was separated and stirred over MnO$_2$ for 24 h, then filtered and dried with anhydrous MgSO$_4$. Remove the solution to get the crude product then further purified by column chromatography on silica gel with dichloromethane as eluent. 2-(2-methoxyphenyl)-1,10-phenanthroline was obtained as a yellow oil (5.3 g, 35% yield). 1H NMR (CDCl$_3$, 400 MHz): chemical shift (ppm) 9.27 (d, 1H), 8.35 (d, 1H), 8.22 (d, 1H), 8.17 (d, 1H), 7.87 (d, 1H), 7.82 (d, 1H), 7.69 (t, 1H), 7.43 (t, 1H), 7.15 (t, 1H), 7.03 (d, 1H), 3.89 (s, 3H).

Synthesis of 9-(2-methoxyphenyl)-1,10-phenanthroline-1-oxide

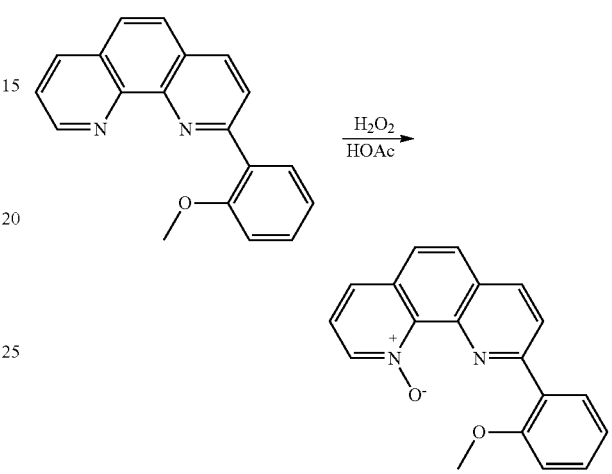

A mixture of 3 g (0.01 mmol) of 2-(2-methoxyphenyl)-1,10-phenanthroline and hydrogen peroxide (0.2 mol), and acetic acid (30 ml) then heated at 80° C. for 3 h. After finishing the reaction, the mixture was allowed to cool to room temperature then poured into the ice water. The reaction mixture was extracted with dichloromethane, dried with anhydrous MgSO$_4$, the solvent was removed and to afforded crude product (2.9 g, 96% yield), and then used in next step without purification.

Synthesis of 2-chloro-9-(2-methoxyphenyl)-1,10-phenanthroline

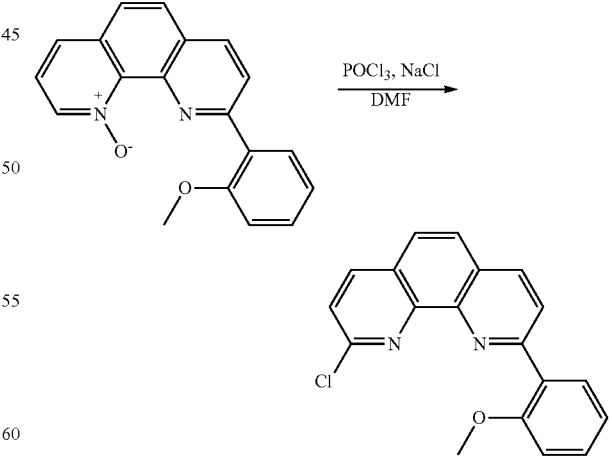

A mixture of 2.9 g (0.01 mmol) of 9-(2-methoxyphenyl)-1,10-phenanthroline-1-oxide and 14.5 g of sodium chloride, and DMF (15 ml). 4.6 ml (0.05 mmol) of phosphoryl chloride was dropwised into then reflux 2 h. The reaction was poured into ice and filtered to get the crude. The crude was purified by column chromatography on silica to afforded product as a yellow solid (0.7 g, 22% yield). 1H NMR (CDCl$_3$, 400 MHz): chemical shift (ppm) 8.22-8.25 (m, 3H), 8.17 (d, 1H), 7.82 (d, 1H), 7.75 (d, 1H), 7.66 (d, 1H), 7.41 (t, 1H), 7.16 (t, 1H), 7.02 (d, 1H), 3.89 (s, 3H). MS (m/z, EI$^+$): 321.1.

Synthesis of 2-(3-(9H-carbazol-9-yl)phenyl)-9-(2-methoxyphenyl)-1,10-phenanthroline

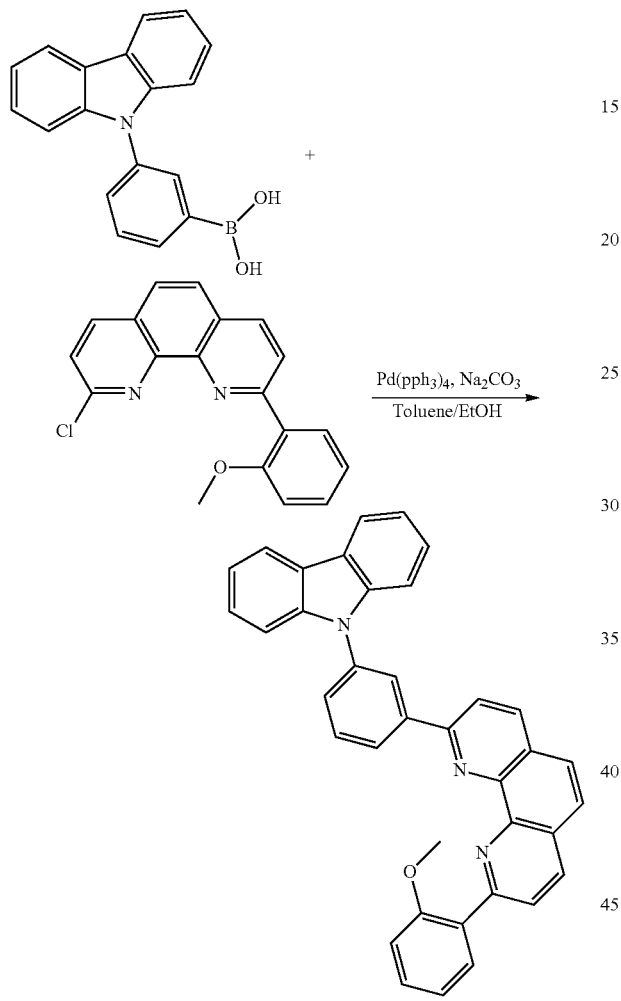

Synthesis of 2-(9-(3-(9H-carbazol-9-yl)phenyl)-1,10-phenanthrolin-2-yl)phenol

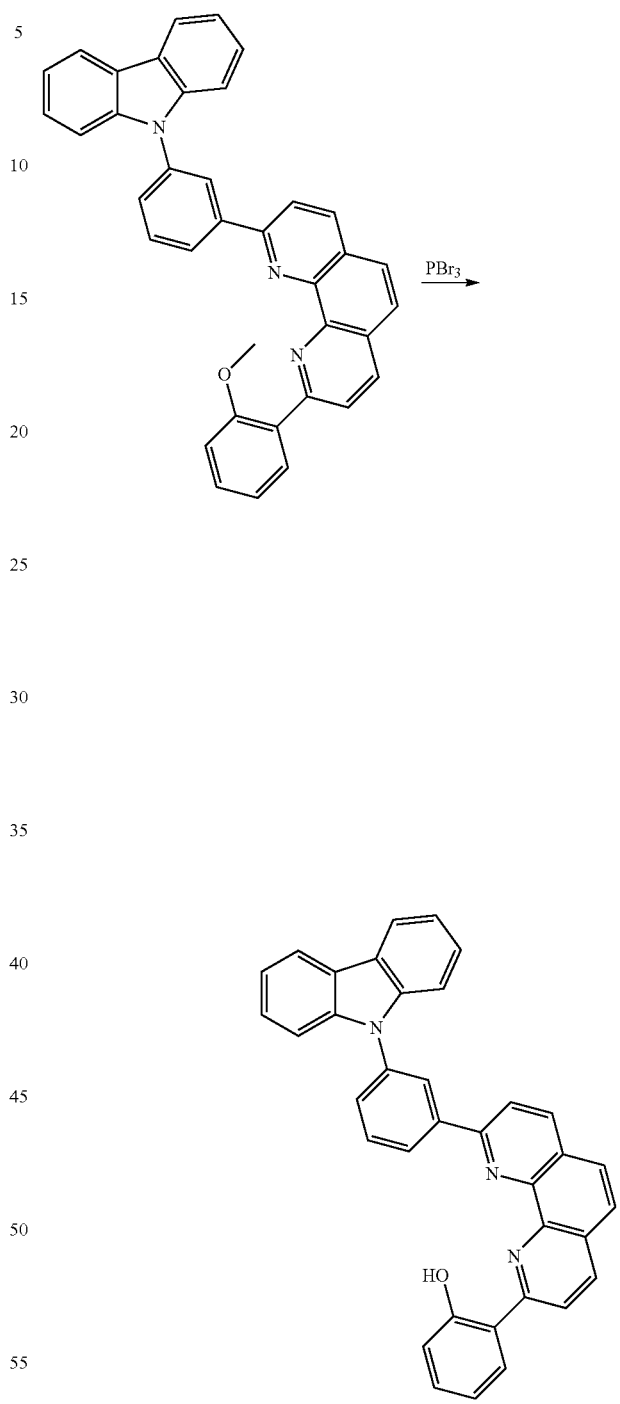

A mixture of 2 g (6.2 mmol) of 2-chloro-9-(2-methoxyphenyl)-1,10-phenanthroline, 2.1 g (7.4 mmol) of 3-(9H-carbazol-9-yl)phenylboronic acid, 0.22 g (0.2 mmol) of Pd(PPh$_3$)$_4$, 3.1 ml of 2M Na$_2$CO$_{3(aq)}$, 10 ml of EtOH and 20 ml toluene was degassed and placed under nitrogen, and then heated at 100° C. for 12 h. After finishing the reaction, the mixture was allowed to cool to room temperature. The organic layer was extracted with dichloromethane and water, dried with anhydrous MgSO$_4$, the solvent was removed and the residue was purified by column chromatography on silica to give product (1.8 g, 55% yield) as a yellow solid. 1H NMR (CDCl$_3$, 400 MHz): chemical shift (ppm) 8.60 (dd, 1H), 8.50 (d, 1H), 8.10-8.32 (m, 7H), 7.75~7.81 (m, 3H), 7.64 (d, 1H), 7.51 (d, 1H), 7.3~7.41 (m, 3H), 7.27 (t, 2H) 6.95 (dd, 2H), 3.89 (s, 3H). MS (m/z, EI$^+$): 527.1.

A mixture of 1 g (1.9 mmol) of 2-(3-(9H-carbazol-9-yl)phenyl)-9-(2-methoxyphenyl)-1,10-phenanthroline and Dichloromethane (20 ml) was prepared. Phosphorus tribromide was added dropwise thereto and then the mixture was stirred for 2 h until the reaction finished. The reaction mixture was extracted with dichloromethane and water, dried with anhydrous MgSO$_4$, the solvent was removed to give crude (0.63 g, 65%). MS (m/z, EI$^+$): 514.2.

Synthesis of 2-(9-(3-(9H-carbazol-9-yl)phenyl)-1,10-phenanthrolin-2-yl)phenol, lithium salt (C1)

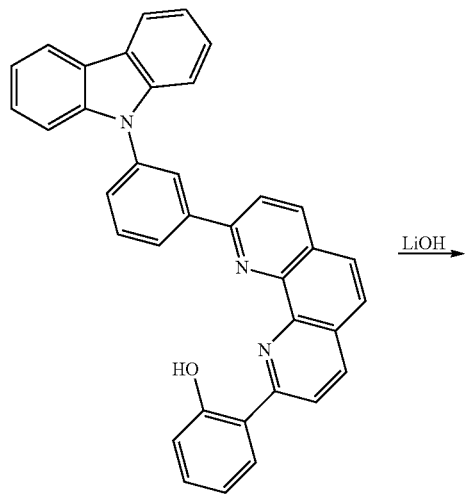

An ethanol solution (80 ml) of 2-(9-(3-(9H-carbazol-9-yl)phenyl)-1,10-phenanthrolin-2-yl)phenol (1 g, 1.9 mmol) was slowly added to an ethanol solution (5 ml) of lithium hydroxide monohydrate (0.8 g, 1.50 mmol), and the mixture was stirred at room temperature. After 4 h, the solvent was in vacuum to give a yellow solid. The obtained yellow solid was purified with sublimation to give compound C1 (0.5 g, 48% yield). 1H NMR (CDCl$_3$, 400 MHz): chemical shift (ppm) 8.60 (dd, 1H), 8.50 (d, 1H), 8.10-8.32 (m, 7H), 7.74-7.82 (m, 3H), 7.64 (d, 1H), 7.50 (d, 1H), 7.32-7.41 (m, 3H), 7.25 (t, 2H) 6.81-6.96 (dd, 2H). MS (m/z, EI$^+$): 519.2.

Example 2

Synthesis of C5

Synthesis of 2-(9-(3-isopropyl-5-(3-isopropyl-9H-carbazol-9-yl)phenyl)-1,10-phenanthrolin-2-yl)phenol, lithium salt 3-isopropyl-5-(3-isopropyl-9H-carbazol-9-yl)phenylboronic acid instead of 3-(9H-carbazol-9-yl)phenylboronic acid, except for using the same method as in synthesis Example 1, the desired compound of 2-(9-(3-isopropyl-5-(3-isopropyl-9H-carbazol-9-yl)phenyl)-1,10-phenanthrolin-2-yl)phenol, lithium salt (C5) was obtained. MS (m/z, EI$^+$): 604.6.

Example 3

Synthesis of C13

Synthesis of 2-(9-(3-(9H-3,9'-bicarbazol-9-yl)phenyl)-1,10-phenanthrolin-2-yl)phenol, lithium salt 3-(9H-3,9'-bicarbazol-9-yl)phenylboronic acid instead of 3-(9H-carbazol-9-yl)phenylboronic acid, except for using the same method as in synthesis Example 1, the desired compound of 2-(9-(3-(9H-3,9'-bicarbazol-9-yl)phenyl)-1,10-phenanthrolin-2-yl)phenol, lithium salt (C13) was obtained. MS (m/z, EI$^+$): 685.3

Example 4

Synthesis of C18

Synthesis of 11-(3-(9-(2-methoxyphenyl)-1,10-phenanthrolin-2-yl)phenyl)-12-phenyl-11,12-dihydroindolo[2,3-a]carbazole

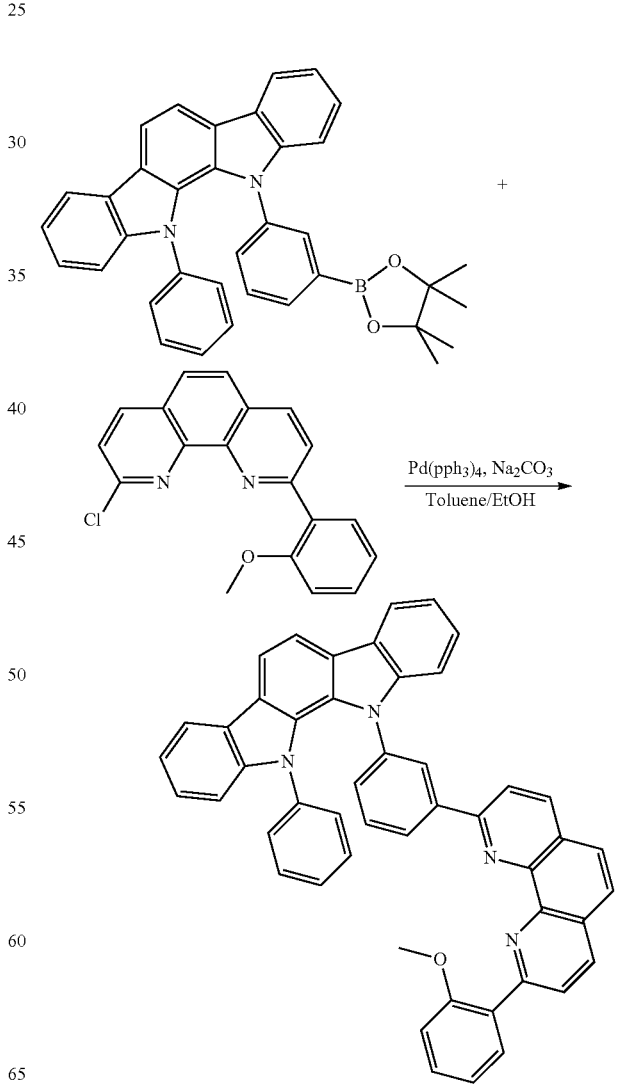

A mixture of 2 g (6.2 mmol) of 2-chloro-9-(2-methoxyphenyl)-1,10-phenanthroline, 3.9 g (7.4 mmol) of 11-phenyl-12-(3-(4,4,5,5-tetramethyl-1,3,2-dioxaborolan-2-yl)phenyl)-11,12-dihydroindolo[2,3-a]carbazole, 0.22 g (0.2 mmol) of Pd(PPh$_3$)$_4$, 3.1 ml of 2M Na$_2$CO$_{3(aq)}$, 12 ml of EtOH and 24 ml toluene was degassed and placed under nitrogen, and then heated at 100° C. for 12 h. After finishing the reaction, the resulting mixture was allowed to cool to room temperature, then an organic layer was extracted therefrom using dichloromethane and water, and dried with anhydrous MgSO$_4$, the solvent was removed and the residue was purified by column chromatography on silica to give product (1.8 g, 44%) as a yellow solid. MS (m/z, EI$^+$): 693.8.

Synthesis of 2-(9-(3-(12-phenylindolo[2,3-a]carbazol-11(12H)-yl)phenyl)-1,10-phenanthrolin-2-yl)phenol

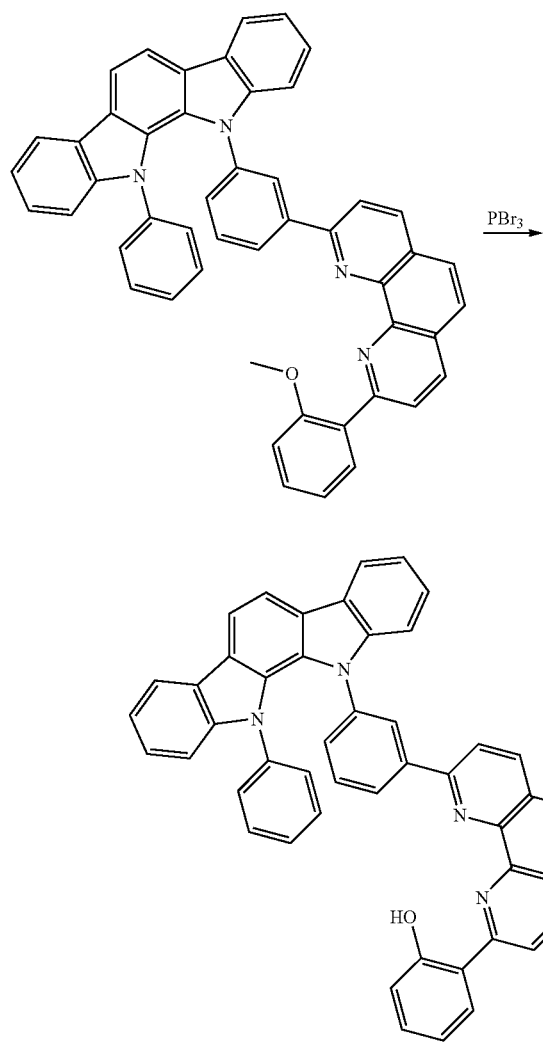

A mixture of 1.8 g (2.6 mmol) of 11-(3-(9-(2-methoxyphenyl)-1,10-phenanthrolin-2-yl)phenyl)-12-phenyl-11,12-dihydroindolo[2,3-a]carbazole and dichloromethane (30 ml) was prepared. Phosphorus tribromide was dropwise thereto then stirred for 2 h until the reaction finished. The reaction mixture was extracted with dichloromethane and water, dried with anhydrous MgSO$_4$, the solvent was removed to give crude (0.91 g, 51% yield). MS (m/z, EI$^+$): 679.1.

Synthesis of 11-(3-(9-(2-methoxyphenyl)-1,10-phenanthrolin-2-yl)phenyl)-12-phenyl-11,12-dihydroindolo[2,3-a]carbazole, lithium salt

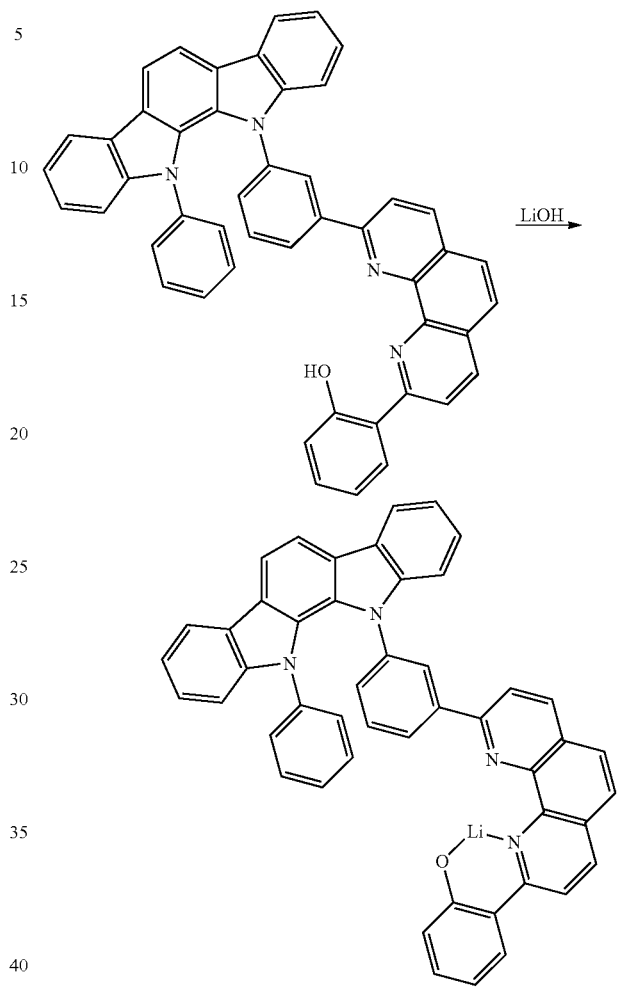

A ethanol solution (180 ml) of a 2-(9-(3-(12-phenylindolo[2,3-a]carbazol-11(12H)-yl)phenyl)-1,10-phenanthrolin-2-yl)phenol (0.91 g, 1.3 mmol) was slowly added to a ethanol solution (5 ml) of lithium hydroxide monohydrate (0.05 g, 1.3 mmol), and the mixture was stirred at room temperature. After 4 h, the solvent was evaporated in vacuum to give a yellow solid. The obtained solid were purified with sublimation to give compound C18 (0.34 g, 38% yield). MS (m/z, EI$^+$): 685.5.

Example 5

Synthesis of C19

Synthesis of 1-(3-(9-(2-methoxyphenyl)-1,10-phenanthrolin-2-yl)phenyl)-3,3-dimethyl-1,3-dihydroindeno[2,1-b]carbazole 3,3-dimethyl-1-(3-(4,4,5,5-tetramethyl-1,3,2-dioxaborolan-2-yl)phenyl)-1,3-dihydroindeno[2,1-b]carbazole instead of 11-phenyl-12-(3-(4,4,5,5-tetramethyl-1,3,2-dioxaborolan-2-yl)phenyl)-11,12-dihydroindolo[2,3-a]carbazole, except for using the same method as in synthesis Example 4, the desired compound of 1-(3-(9-(2-methoxyphenyl)-1, 10-phenanthrolin-2-yl)phenyl)-3,3-dimethyl-1,3-dihydroindeno[2,1-b]carbazole (C19) was obtained. MS (m/z, EI+): 644.8.

Example 6

Synthesis of C28

Synthesis of 2-(2-methoxyphenyl)-9-(4-(10-(naphthalen-1-yl) anthracen-9-yl)phenyl)-1,10-phenanthroline

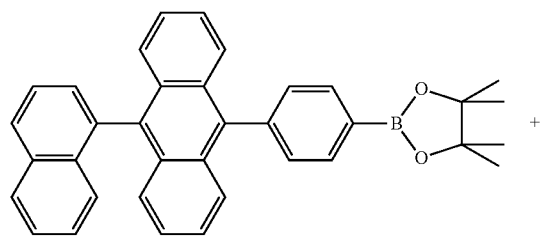

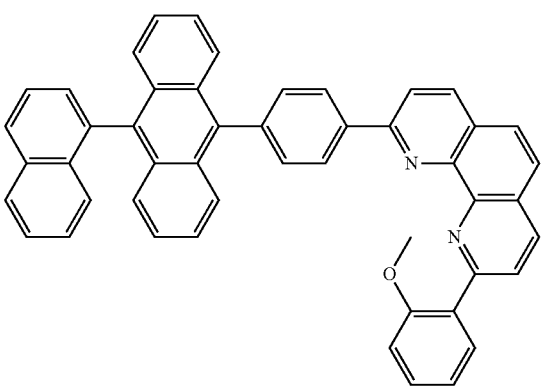

A mixture of 2 g (6.2 mmol) of 2-chloro-9-(2-methoxyphenyl)-1,10-phenanthroline, 3.7 g (7.4 mmol) of 4,4,5,5-tetramethyl-2-(4-(10-(naphthalene-1-yl)anthracen-9-yl)phenyl)-1,3,2-dioxaborolane, 0.22 g (0.2 mmol) of Pd(PPh$_3$)$_4$, 3.1 ml of 2M Na$_2$CO$_{3(aq)}$, 10 ml of EtOH and 20 ml toluene was degassed and placed under nitrogen, and then heated at 100° C. for 12 h. After finishing the reaction, the mixture was allowed to cool to room temperature, then an organic layer was extracted therefrom using dichloromethane and water and dried with anhydrous MgSO$_4$ to remove solvent to form a residue. The residue was purified by column chromatography on silica to give product (2.1 g, 53% yield) as a yellow solid. MS (m/z, EI+): 664.7.

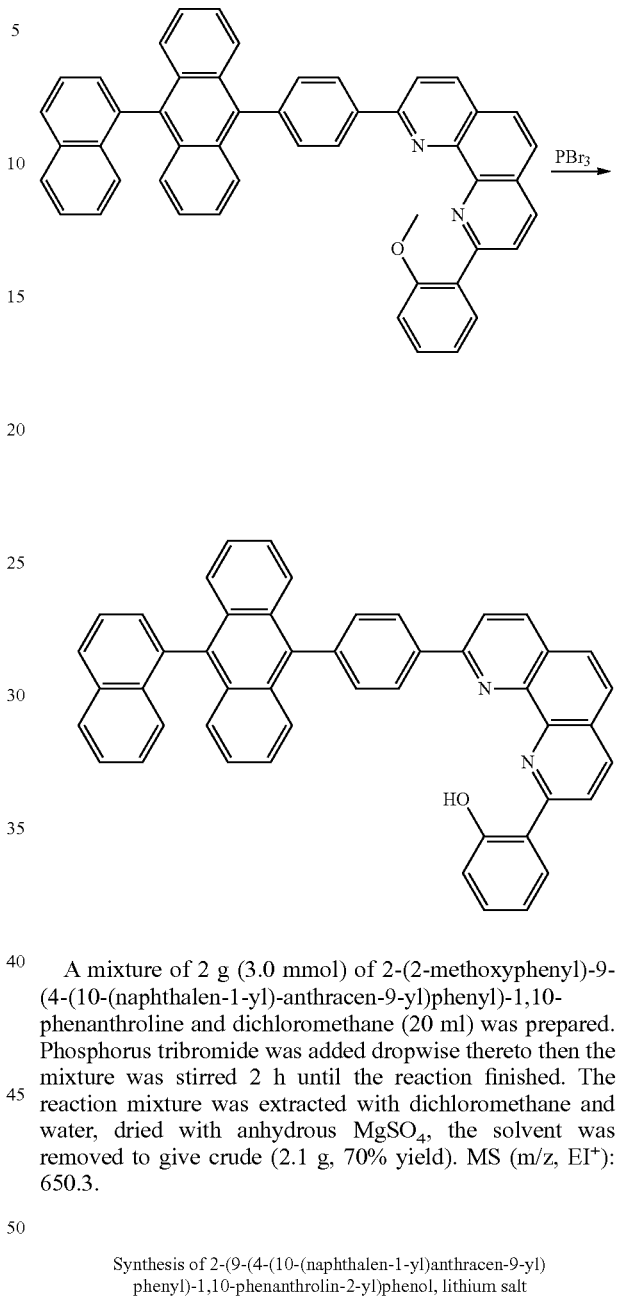

Synthesis of 2-(9-(4-(10-(naphthalene-1-yl)anthracen-9-yl)phenyl)-1,10-phenanthrolin-2-yl)phenol A mixture of 2 g (3.0 mmol) of 2-(2-methoxyphenyl)-9-(4-(10-(naphthalen-1-yl)-anthracen-9-yl)phenyl)-1,10-phenanthroline and dichloromethane (20 ml) was prepared. Phosphorus tribromide was added dropwise thereto then the mixture was stirred 2 h until the reaction finished. The reaction mixture was extracted with dichloromethane and water, dried with anhydrous MgSO$_4$, the solvent was removed to give crude (2.1 g, 70% yield). MS (m/z, EI+): 650.3.

Synthesis of 2-(9-(4-(10-(naphthalen-1-yl)anthracen-9-yl)phenyl)-1,10-phenanthrolin-2-yl)phenol, lithium salt

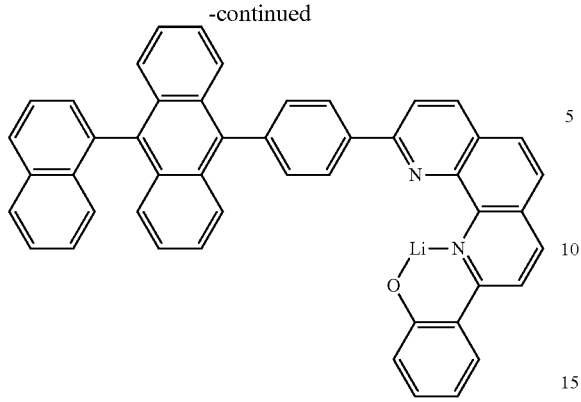

An ethanol solution (200 ml) of 2-(9-(4-(10-(naphthalen-1-yl) anthracen-9-yl)phenyl)-1,10-phenanthrolin-2-yl)phenol (1 g, 1.9 mmol) was slowly added to an ethanol solution (5 ml) of lithiumhydroxide monohydrate (0.06 g, 1.9 mmol), and the mixture was stirred at room temperature. After 4 h, the solvent was evaporated in vacuum to give a yellow solid. The obtained solid was purified with sublimation to give the compound C28 (0.56 g, 56% yield). MS (m/z, EI+): 657.7.

Example 7

Synthesis of C35

Synthesis of 2-(9-(4-(10-phenylanthracen-9-yl)naphthalen-1-yl)-1,10-phenanthrolin-2-yl)phenol, lithium salt 4,4,5,5-tetramethyl-2-(4-(10-phenylanthracen-9-yl)naphthalene-1-yl)-1,3,2-dioxaborolane instead of 4,4,5,5-tetramethyl-2-(4-(10-(naphthalene-1-yl)anthracen-9-yl)phenyl)-1,3,2-dioxaborolane, except for using the same method as in synthesis Example 6, the desired compound of 2-(9-(4-(10-phenylanthracen-9-yl)naphthalen-1-yl)-1,10-phenanthrolin-2-yl) phenol, lithium salt (C35) was obtained. MS (m/z, EI+): 655.9.

Example 8

Synthesis of C38

Synthesis of 2-(2-methoxyphenyl)-9-(4-(triphenylen-2-yl)phenyl)-1,10-phenanthroline

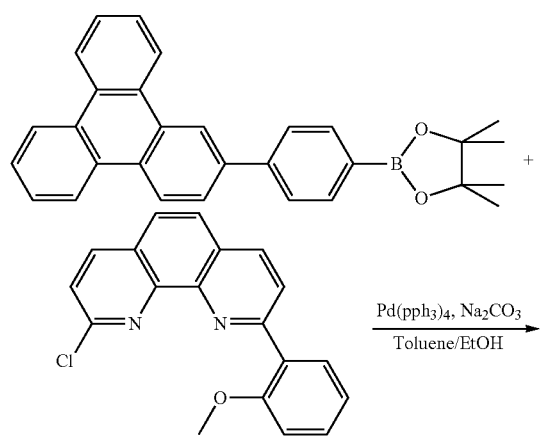

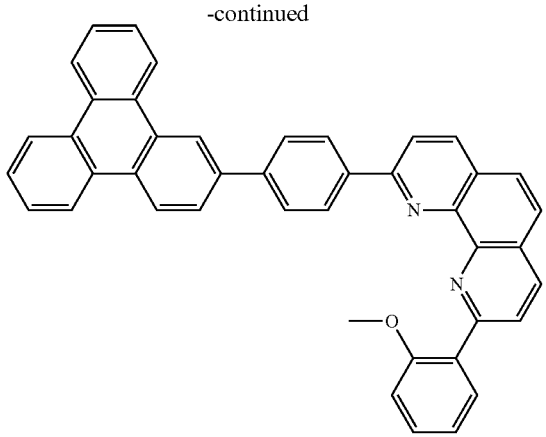

A mixture of 2 g (6.2 mmol) of 2-chloro-9-(2-methoxyphenyl)-1,10-phenanthroline, 3.6 g (7.4 mmol) of 4,4,5,5-tetramethyl-2-(4-(triphenylen-2-yl)phenyl)-1,3,2-dioxaborolane, 0.22 g (0.2 mmol) of Pd(PPh₃)₄, 3.1 ml of 2M Na₂CO₃₍aq₎, 20 ml of EtOH and 40 ml toluene was degassed and placed under nitrogen, and then heated at 100° C. for 12 h. After finishing the reaction, the mixture was allowed to cool to room temperature, then an organic layer was extracted therefrom using dichloromethane and water and dried with anhydrous MgSO₄ to remove solvent to form a residue. The residue was purified by column chromatography on silica to give product (2.2 g, 70% yield) as a yellow solid. MS (m/z, EI+): 588.7.

Synthesis of 2-(9-(4-(triphenylen-2-yl)phenyl)-1,10-phenanthrolin-2-yl)phenol

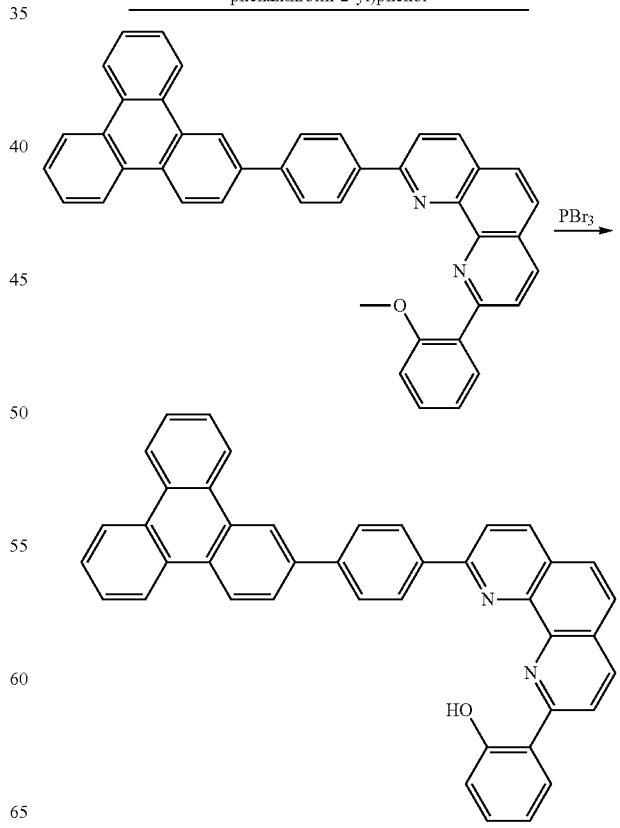

A mixture of 2.2 g (3.0 mmol) of 2-(2-methoxyphenyl)-9-(4-(triphenylen-2-yl)phenyl)-1,10-phenanthrolineline and dichloromethane (20 ml) was prepared. Phosphorus tribromide was added dropwise thereto and then the mixture was stirred for 2 h until the reaction finished. The reaction mixture was extracted with dichloromethane and water, dried with anhydrous MgSO$_4$, and the solvent was removed to give crude (1.5 g, 66% yield). MS (m/z, EI$^+$): 574.7.

Synthesis of 2-(9-(4-(triphenylen-2-yl)phenyl)-1,10-phenanthrolin-2-yl)phenol, lithium salt

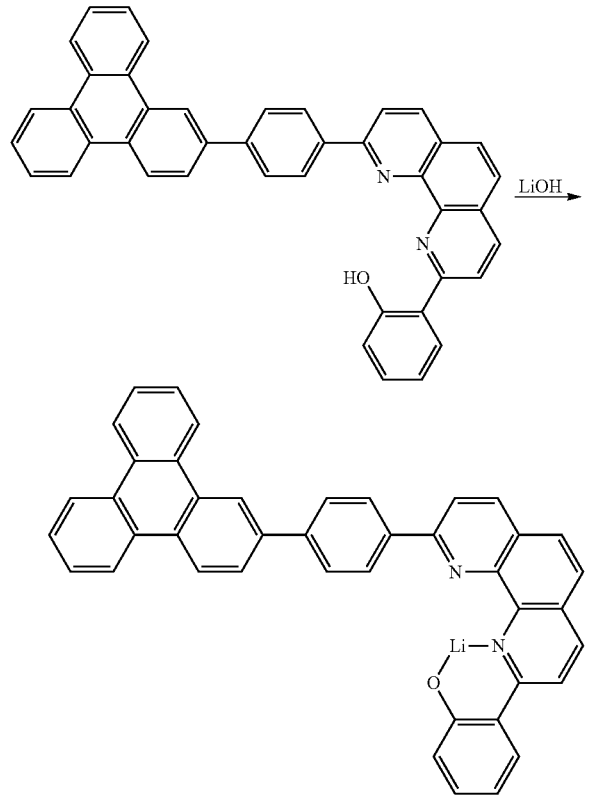

An ethanol solution (300 ml) of a 2-(9-(4-(10-(naphthalen-1-yl) anthracen-9-yl)phenyl)-1,10-phenanthrolin-2-yl) phenol (1.5 g, 2.6 mmol) was slowly added to a ethanol solution (10 ml) of lithium hydroxide monohydrate (0.1 g, 2.6 mmol), and the mixture was stirred at room temperature. After 4 h, the solvent was evaporated in vacuum to give a yellow solid. The obtained solid were purified with sublimation to give compound C38 (0.56 g, 56%). MS (m/z, EI$^+$): 580.7.

Example 9

Synthesis of C46

Synthesis of 2-(9-(9,9-dimethyl-7-(triphenylen-2-yl)-9H-fluoren-2-yl)-1,10-phenanthrolin-2-yl)phenol, lithium salt 9,9-dimethyl-7-(triphenylen-2-yl)-9H-fluoren-2-ylboronic acid instead of 4,4,5,5-tetramethyl-2-(4-(triphenylen-2-yl)phenyl)-1,3,2-dioxaborolane, except for using the same method as in synthesis Example 8, the desired compound of 2-(9-(9,9-dimethyl-7-(triphenylen-2-yl)-9H-fluoren-2-yl)-1,10-phenanthrolin-2-yl)phenol, lithium salt (C46) was obtained. MS (m/z, EI$^+$): 697.0

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit (10$^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer material in an organic EL device, and N4,N4'-di(biphenyl-4-yl)-N4,N4'-diphenylbiphenyl-4,4'-diamine (HT1) is used as the hole transporting layer, N-(biphenyl-4-yl)-9,9-dimethyl-N-(4'-phenyl biphenyl-4-yl)-9H-fluoren-2-amine (EB2) is used as electron blocking layer material, H1 and H2 are used as phosphorescent host material for comparable examples or standard with the present invention of C1, C5, C13, C18, C19, C28, C35, C38 and C46. The chemical structures of the above-mentioned compounds are shown below:

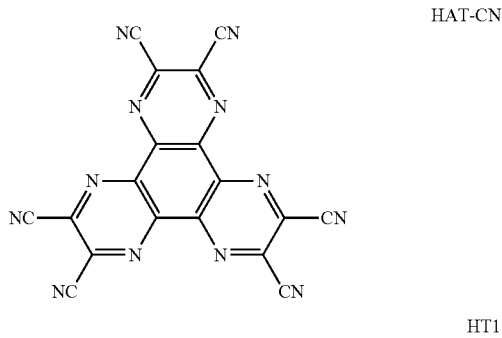

HAT-CN

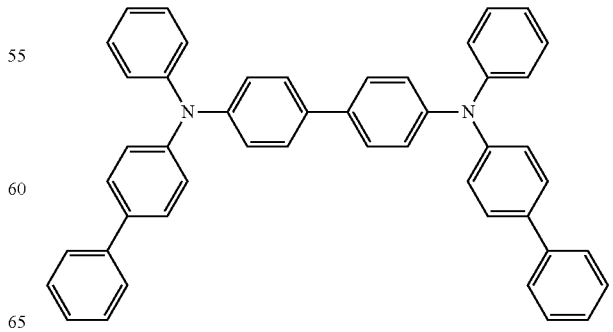

HT1

EB2
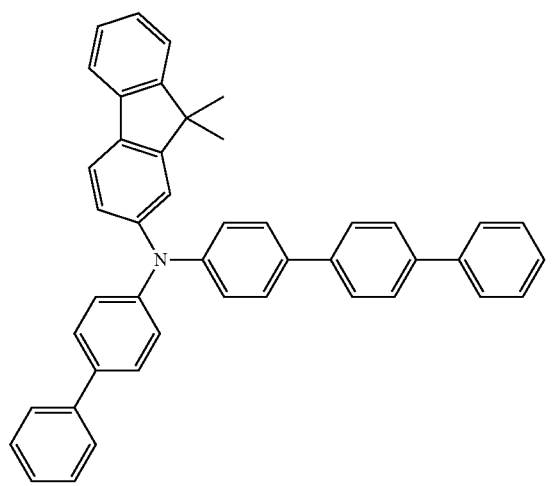
H1
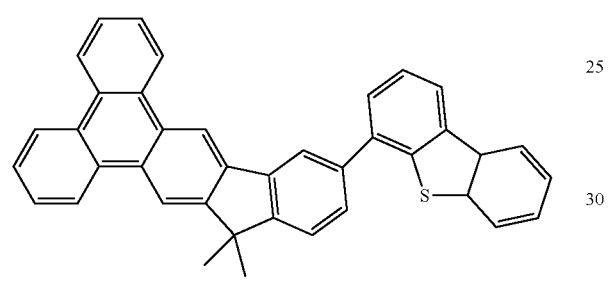
H2
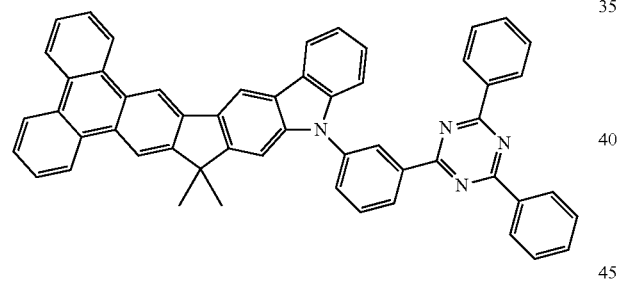
C1
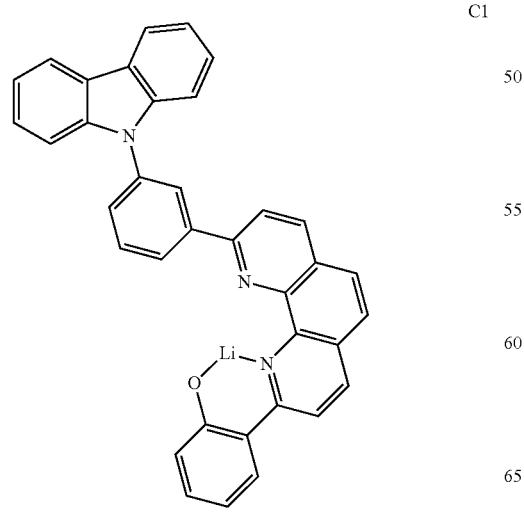
C5
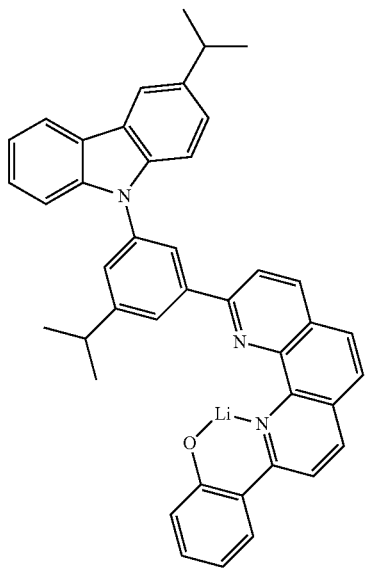
C13
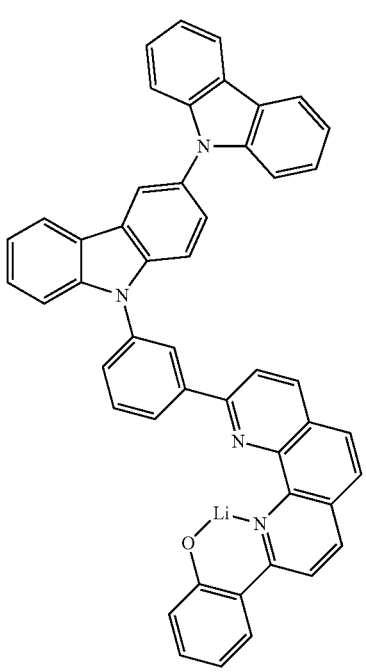

C18
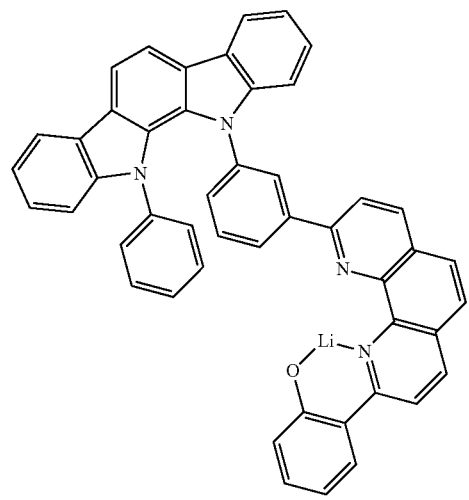
C35
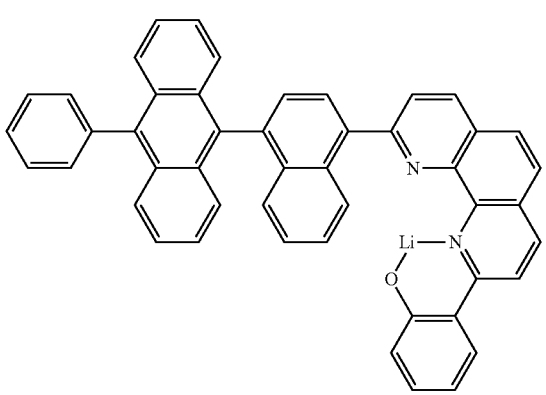
C19
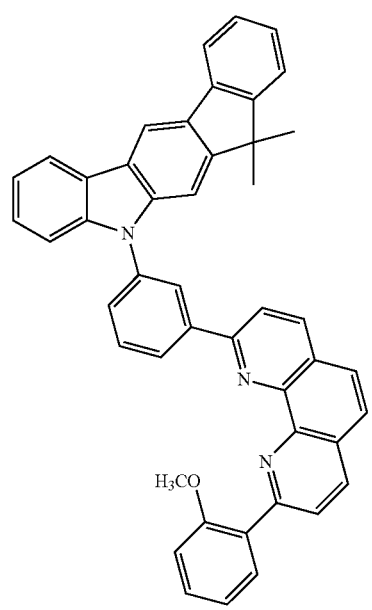
C38
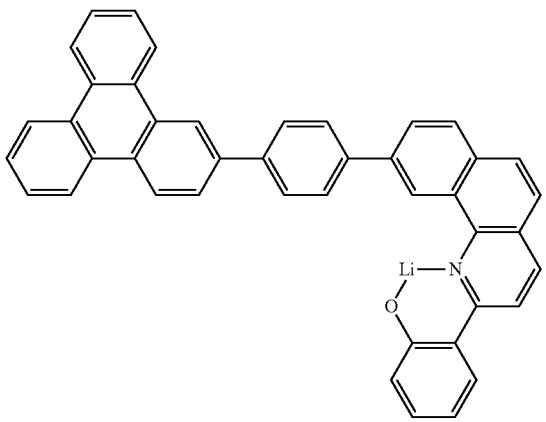
C28
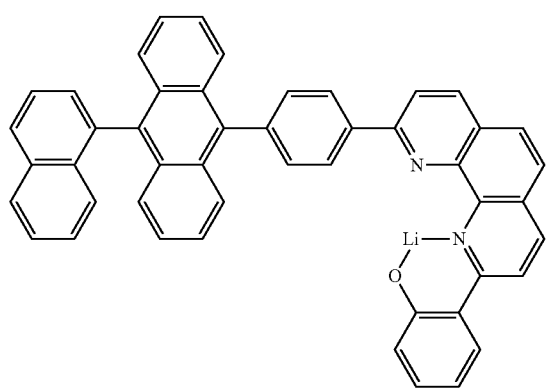
C46
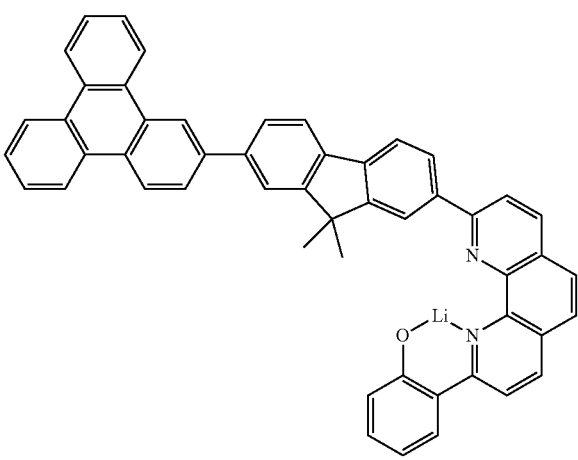
Organic iridium complexes are widely used as phosphorescent dopant for light emitting layer, for example, Ir(ppy)$_3$ can be used for phosphorescent green dopant material of a light emitting layer for an organic EL device.

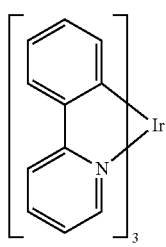

Ir(ppy)₃

HB3 (see the following chemical structure) is used as hole blocking material (HBM) and 2-(10,10-dimethyl-10H-indeno[2,1-b] triphenylen-12-yl)-4,6-diphenyl-1,3,5-triazine (ET2) is used as electron transporting material to co-deposit with 8-hydroxyquinolato-lithium (LiQ) in an organic EL device. The chemical structures of other prior-art OLED materials for producing standard organic EL device control or comparable material for this invention shown as below:

LiQ

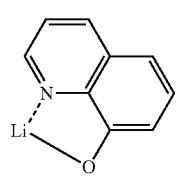

ET2

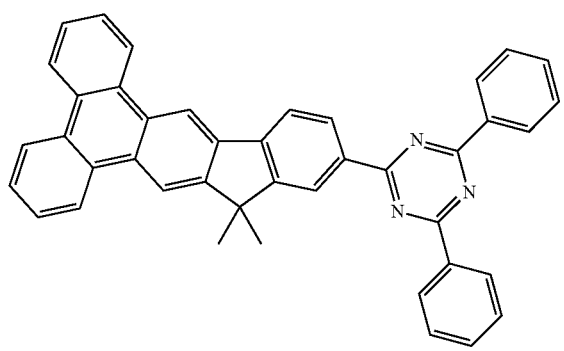

HB3

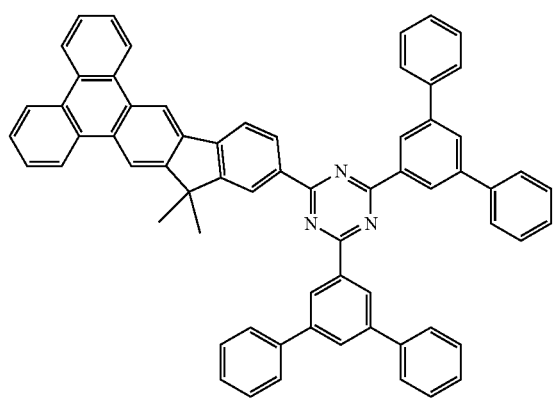

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 10

Using a procedure analogous to the above mentioned general method, a phosphorescent emitting organic EL device having the following device structure was produced (See FIG. 1). Device: ITO/HAT-CN (20 nm)/HT1 (110 nm)/EB2 (5 nm)/phosphorescent emitting host doped 10% Ir(ppy)₃ (30 nm)/HB3(10 nm)/ET2 doped 40% LiQ (35 nm)/LiQ (1 nm)/Al (160 nm). The I-V-B (at 1000 nits) and half-life time of phosphorescent emitting organic EL device testing report is shown in Table 1. The half-life time is defined that the initial luminance of 3000 cd/m² has dropped to half.

TABLE 1

| Emitting host | Voltage (V) | Efficiency (cd/A) | Color | Half-life time (hour) |
|---|---|---|---|---|
| H1 | 4.5 | 25 | green | 280 |
| C1 | 4.7 | 12 | green | 150 |
| C5 | 5.5 | 15 | green | 100 |
| C13 | 4.8 | 17 | green | 200 |
| C18 | 4.2 | 28 | green | 300 |
| C19 | 4.5 | 26 | green | 350 |
| C28 | 7.5 | 10 | green | 130 |
| C35 | 8.5 | 11 | green | 80 |
| C38 | 7.5 | 13 | green | 70 |
| C46 | 8.8 | 9 | green | 100 |

Example 11

Using a procedure analogous to the above mentioned general method, a phosphorescent emitting organic EL device having the following device structure was produced (See FIG. 1). Device: ITO/HAT-CN (20 nm)/HT1 (110 nm)/EB2 (5 nm)/H2 doped 10% Ir(ppy)₃ (30 nm)/hole blocking material (HBM) (10 nm)/electron transport material (ETM) (30 nm)/LiQ (1 nm)/Al (160 nm). The I-V-B (at 1000 nits) and half-life time of the phosphorescent emitting organic EL device testing report is shown in Table 1. The half-life time is defined that the initial luminance of 3000 cd/m² has dropped to half.

TABLE 2

| HBM | ETM | Voltage (V) | Efficiency (cd/A) | Emitting Color | Half-life time (hour) |
|---|---|---|---|---|---|
| HB3 | ET2 | 4.5 | 40 | green | 550 |
| HB3 | C1 | 4.5 | 45 | green | 520 |
| HB3 | C5 | 4.0 | 36 | green | 550 |
| HB3 | C13 | 4.8 | 34 | green | 650 |

TABLE 2-continued

| HBM | ETM | Voltage (V) | Efficiency (cd/A) | Emitting Color | Half-life time (hour) |
|---|---|---|---|---|---|
| HB3 | C18 | 5.5 | 26 | green | 660 |
| HB3 | C19 | 5.2 | 35 | green | 560 |
| HB3 | C28 | 3.8 | 52 | green | 580 |
| HB3 | C35 | 4.1 | 48 | green | 600 |
| HB3 | C38 | 4.0 | 45 | green | 500 |
| HB3 | C46 | 3.8 | 35 | green | 460 |

In the above preferred embodiments for a phosphorescent organic EL device testing report (see Table 1 and Table 2), we show that the phenanthroline-based compound with a general formula (1) used as phosphorescent light emitting host material of a light emitting layer, and/or electron transporting layer material, and/or hole blocking layer material, and/or a thermally activated delayed fluorescence (TADF) material of a light emitting layer for an organic EL device in accordance with the present invention can display good performance than the prior art of organic EL materials.

To sum up, the present invention discloses an phenanthroline-based compound which can be used as phosphorescent light emitting host material of a light emitting layer, and/or electron transporting layer material, and/or hole blocking layer material, and/or thermally activated delayed fluorescence (TADF) material of a light emitting layer for an organic EL device. The phenanthroline-based compound is represented by the following formula (1)

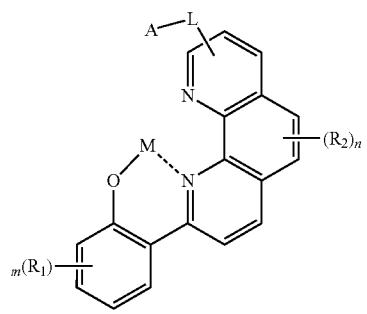

formula (1)

wherein A is selected from the group consisting of formula (2) to formula (8):

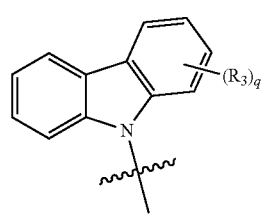

formula (2)

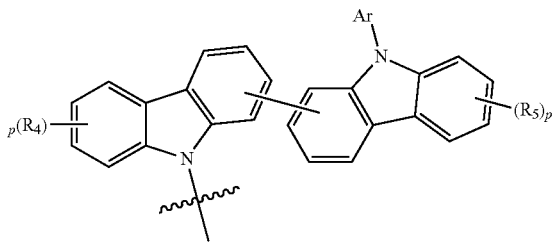

formula (3)

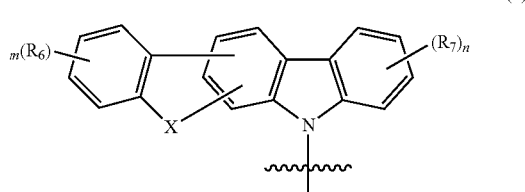

formula (4)

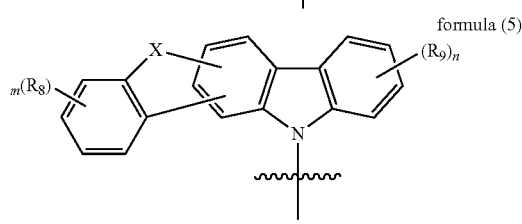

formula (5)

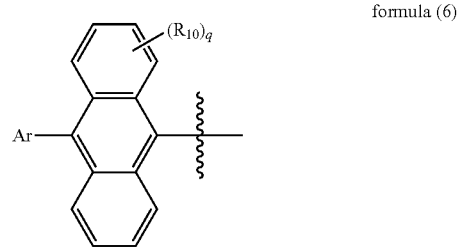

formula (6)

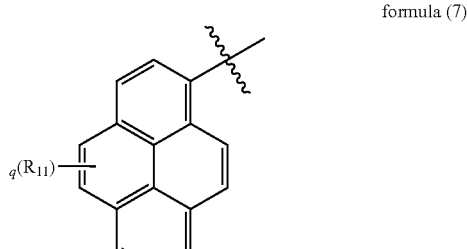

formula (7)

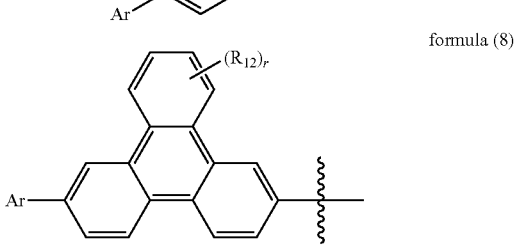

formula (8)

L represents a single bond, a substituted or unsubstituted arylene group having 6 to 30 ring carbon atoms, or a substituted or unsubstituted heterarylene group having 3 to 30 ring carbon atoms, m represent an integer of 0 to 4, n represents an integer of 0 to 6, p represents an integer of 0 to 7, q represents an integer of 0 to 8, r represents an integer of 0 to 10, M represents a metal atom or a non-metal atom; X is a divalent bridge comprising atoms or groups selected from the group consisting of O, S, C(R$_{13}$)(R$_{14}$), NR$_{15}$ and Si(R$_{16}$)(R$_{17}$), Ar is selected from the group consisting of a substituted or unsubstituted aryl group having 6 to 30 carbon atoms and a substituted or unsubstituted heteroaryl group having 3 to 30 carbon atoms, R$_1$ to R$_{17}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. A phenanthroline-based compound is represented by the following formula (1):

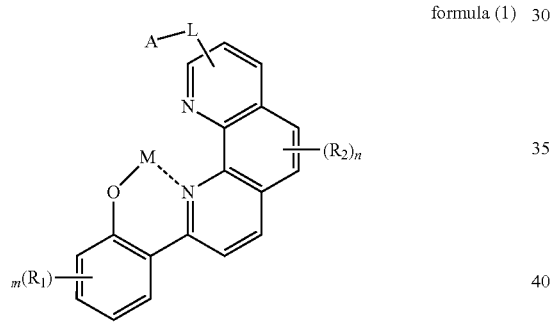

formula (1)

wherein A is selected from the group consisting of formula (2) to formula (8):

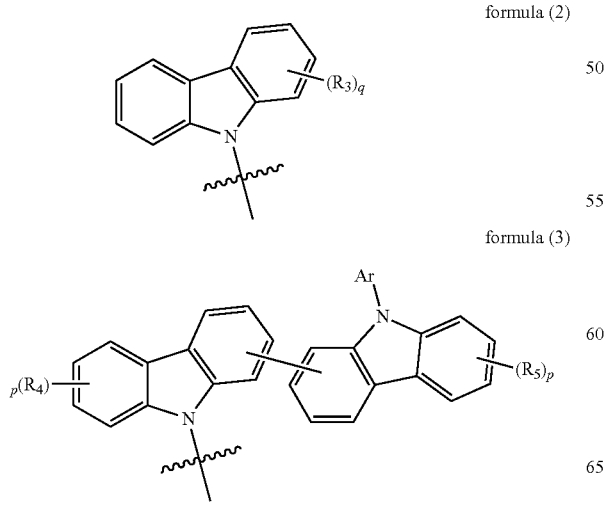

formula (2)

formula (3)

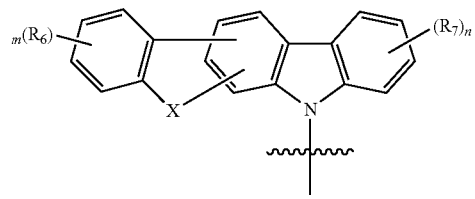

formula (4)

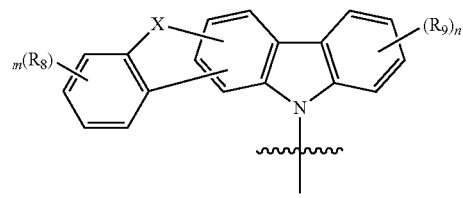

formula (5)

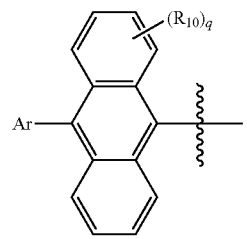

formula (6)

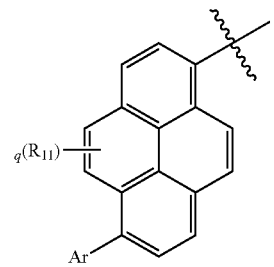

formula (7)

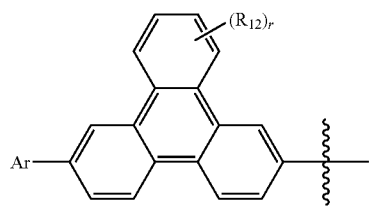

formula (8)

L represents a single bond, a substituted or unsubstituted arylene group having 6 to 30 ring carbon atoms, or a substituted or unsubstituted heterarylene group having 3 to 30 ring carbon atoms, m represent an integer of 0 to 4, n represents an integer of 0 to 6, p represents an integer of 0 to 7, q represents an integer of 0 to 8, r represents an integer of 0 to 10, M represents a metal atom or a non-metal atom or group; X is a divalent bridge comprising atoms or groups selected from the group consisting of O, S, C(R$_{13}$)(R$_{14}$), NR$_{15}$ and Si(R$_{16}$)(R$_{17}$), Ar is selected from the group consisting of a substituted or unsubstituted aryl group having 6 to 30 carbon atoms and a substituted or unsubstituted heteroaryl group having 3 to 30 carbon atoms, R$_1$ to R$_{17}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

2. The phenanthroline-based compound according to claim 1, wherein L is represented by the following formula (9):

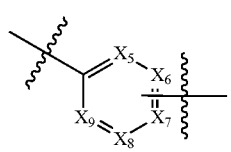

formula (9)

wherein $X_5$ to $X_9$ independently represents a nitrogen atom or $C(R_s)$, and each $R_s$ represents a hydrogen, a halide, a substituted or unsubstituted alkyl group having 1 to 30 carbon atoms, or a substituted or unsubstituted aryl group having 6 to 30 carbon atoms.

3. The phenanthroline-based compound according to claim 1, wherein M represents a metal atom selected from the group consisting of Li, Na, K and Yb.

4. The phenanthroline-based compound according to claim 1, wherein M represents a non-metal atom or group bonded with oxygen, and the non-metal atom or group is selected from the group consisting of hydrogen and an alkyl group having 1 to 30 carbon atoms.

5. The phenanthroline-based compound according to claim 1, wherein the compound is represented by one of the following formulas:

C1

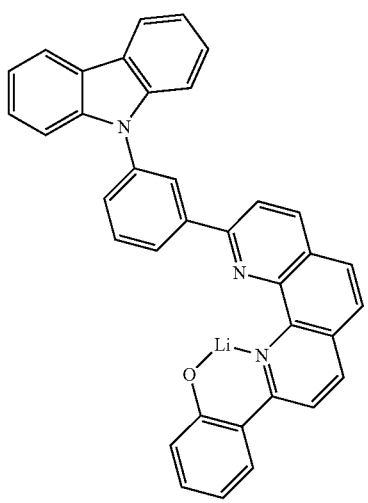

-continued

C2

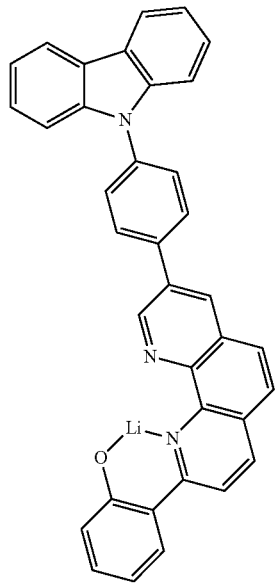

C3

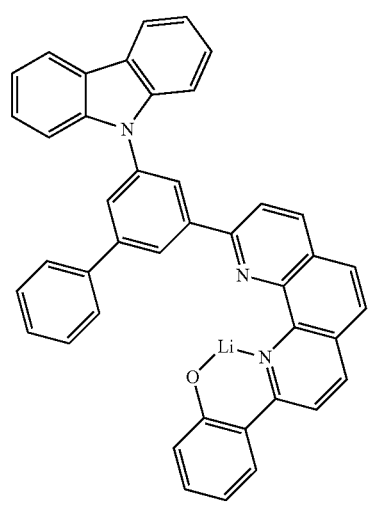

C4

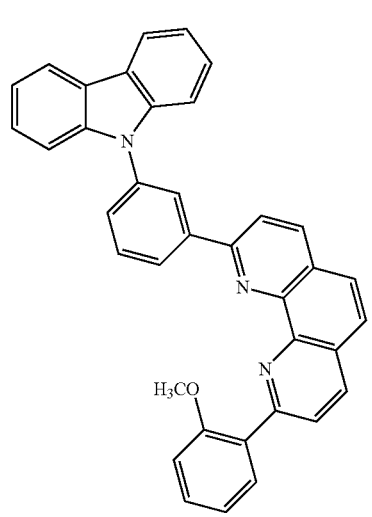

C5
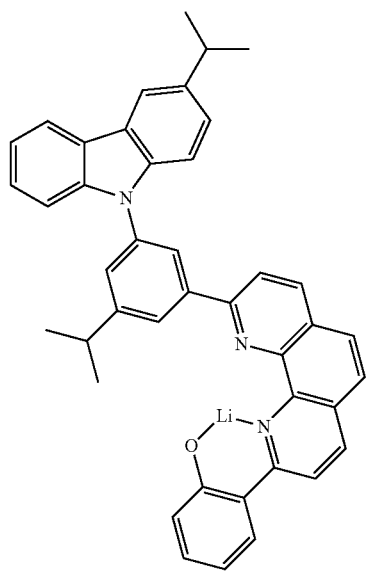
C6
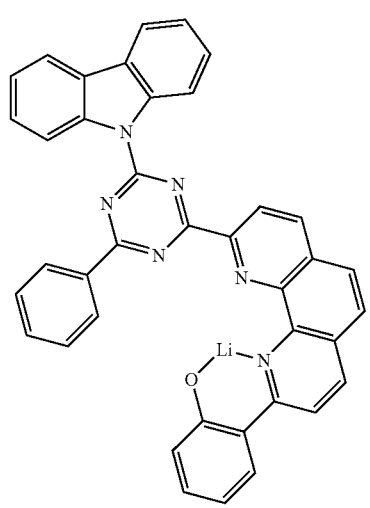
C7
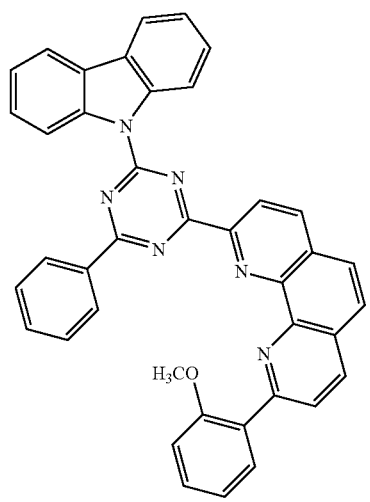
C8
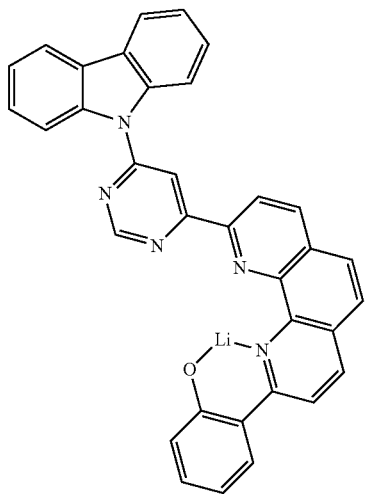
C9
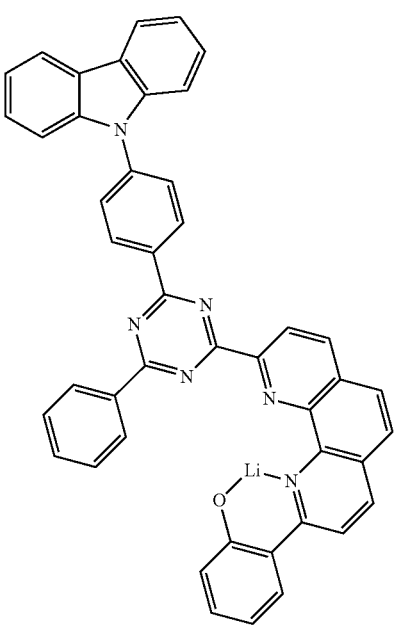
C10
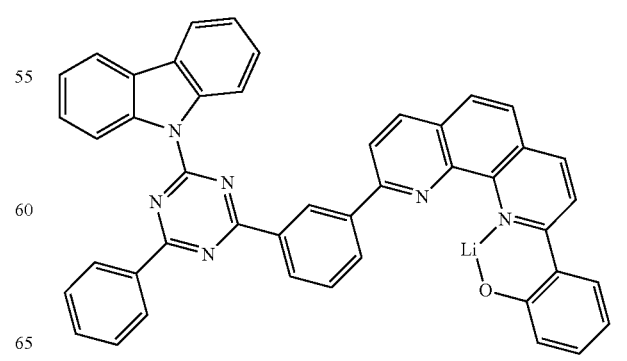

C11
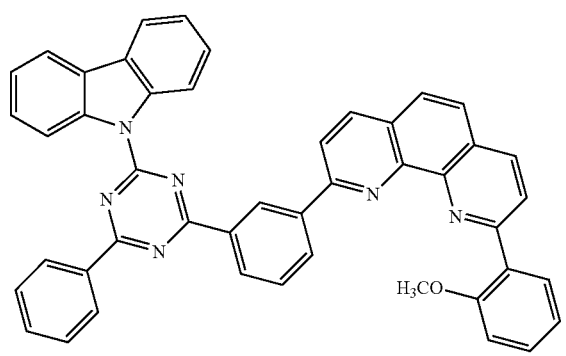
C12
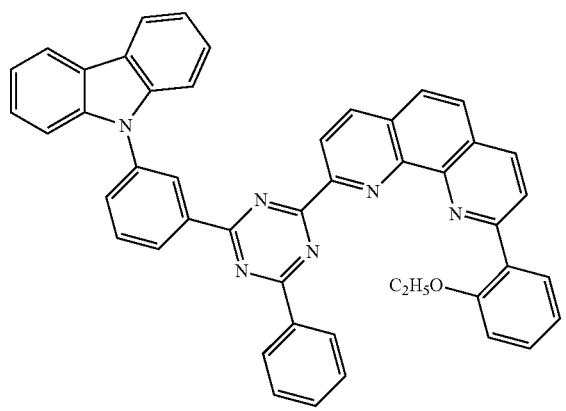
C13
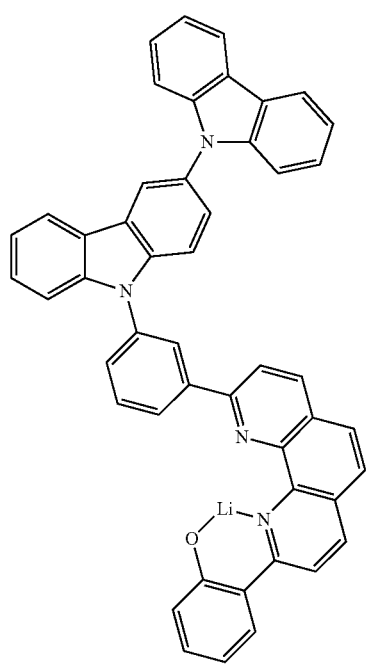
C14
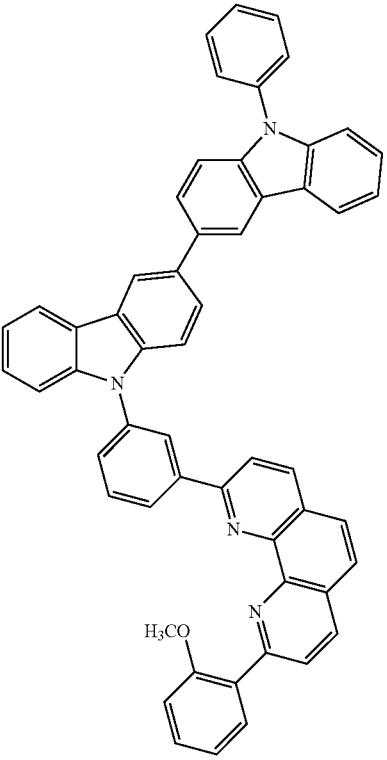
C15
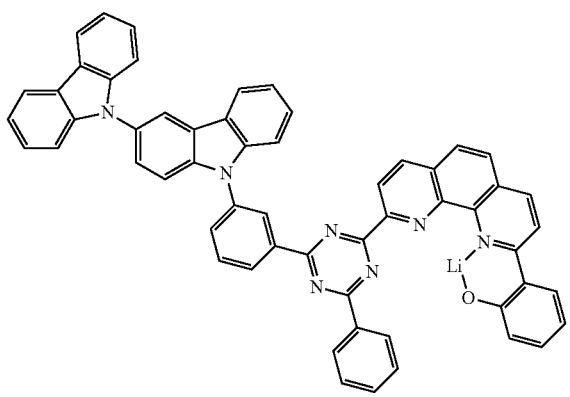
C16
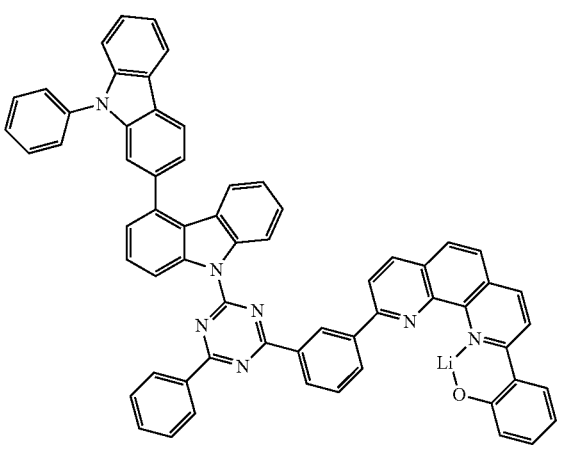

C17
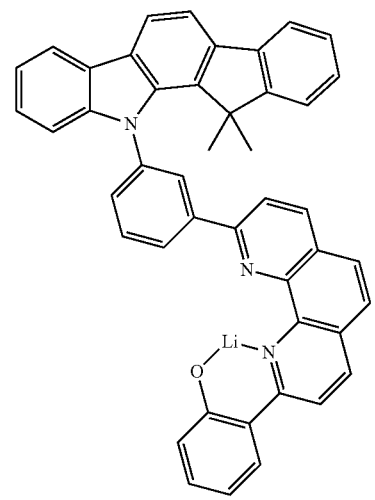
C18
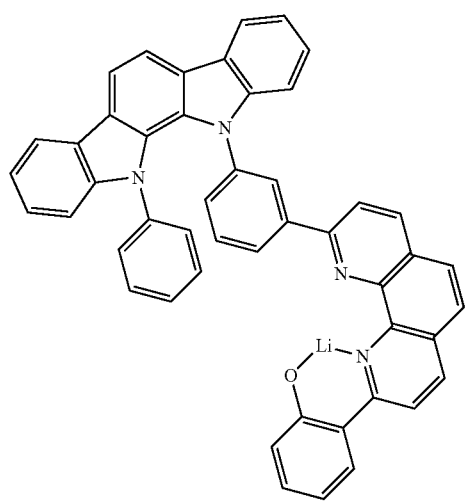
C19
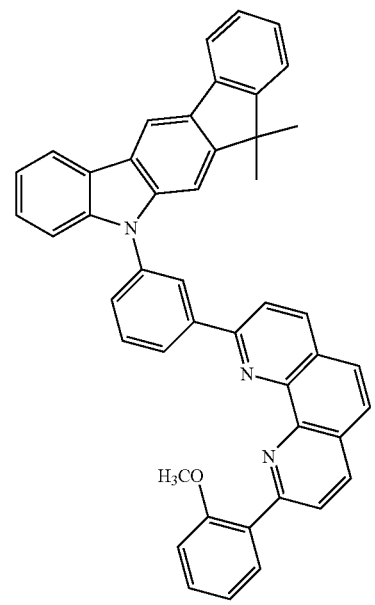
C20
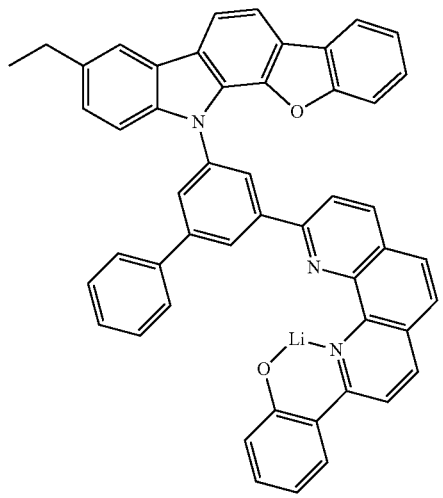
C21
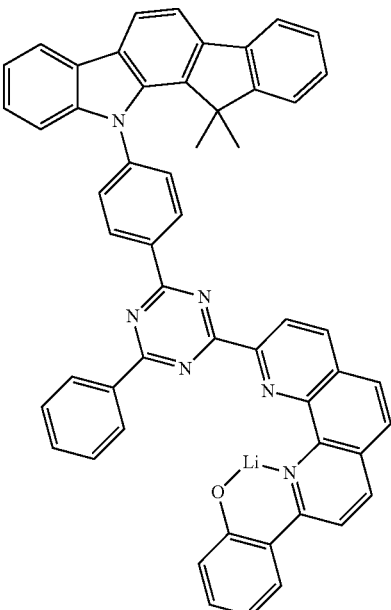
C22
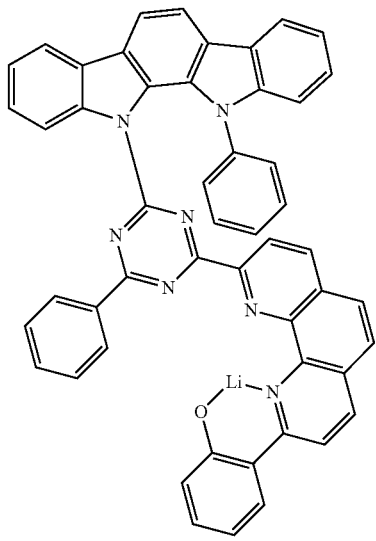

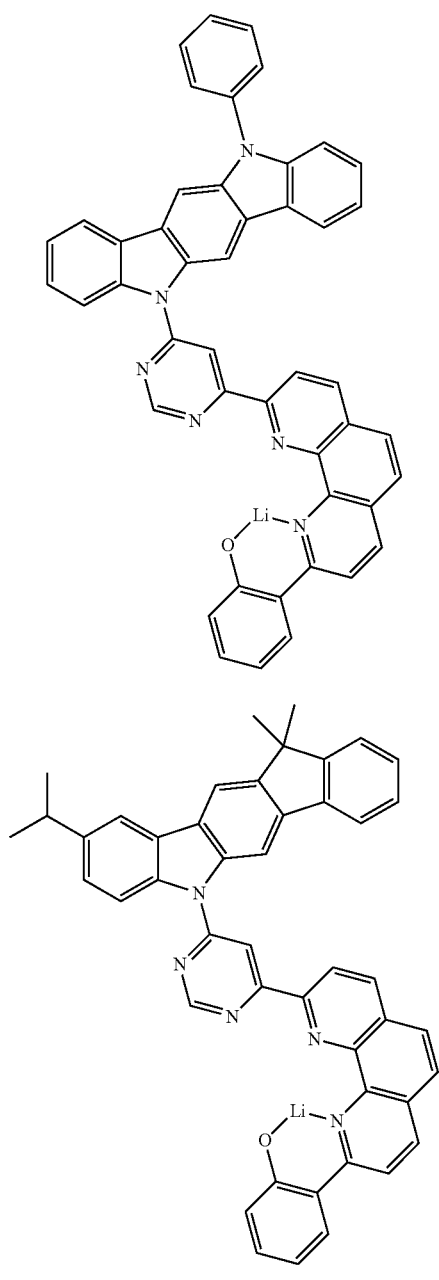
C23
C24
C25
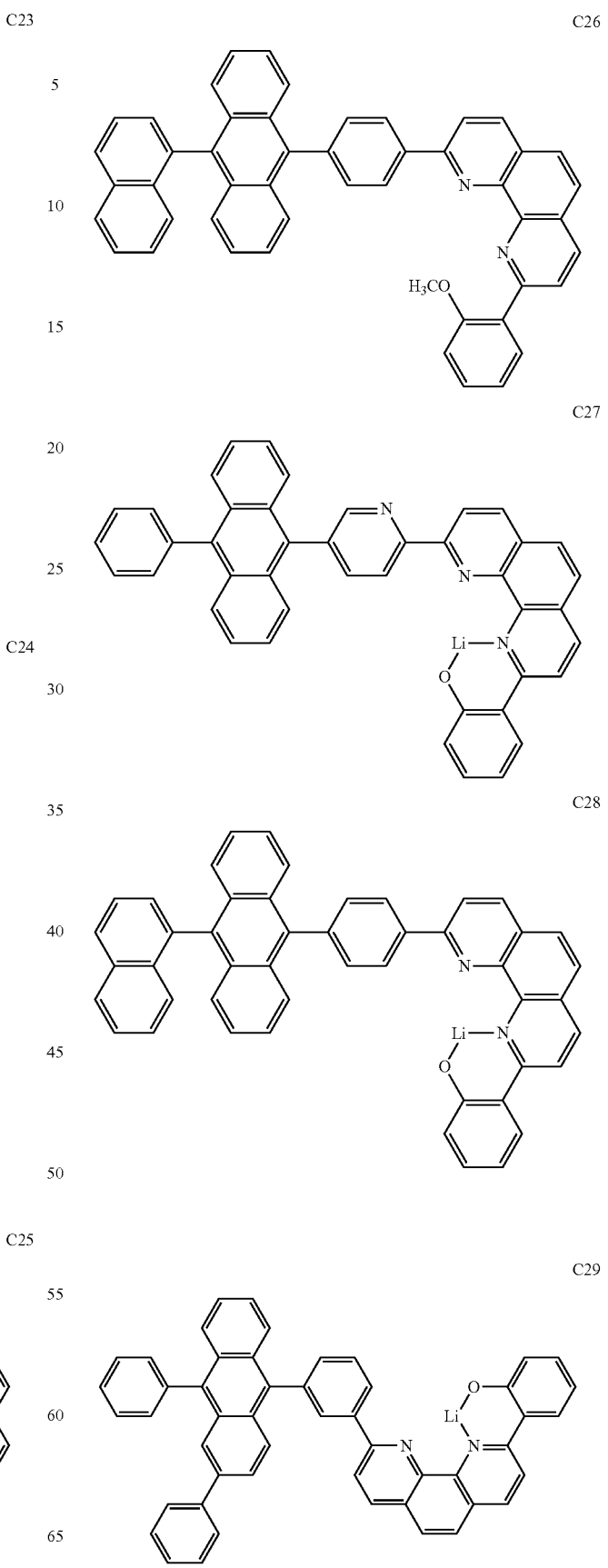
C26
C27
C28
C29

-continued
C30
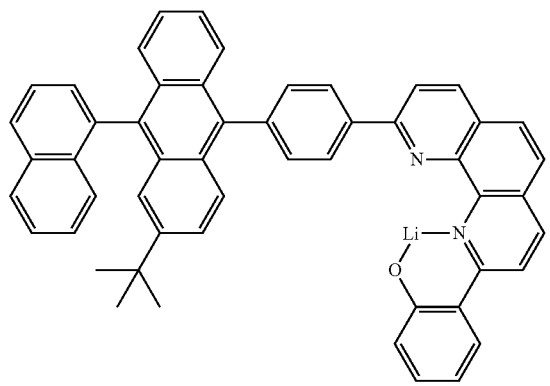
C31
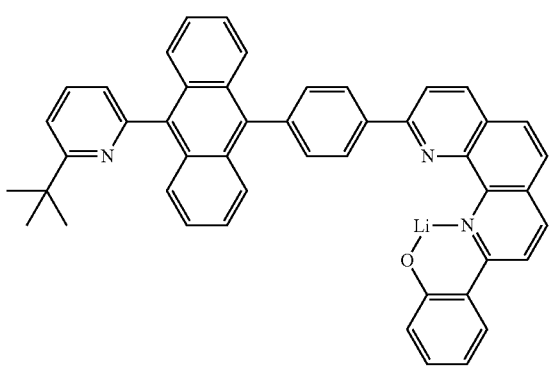
C32
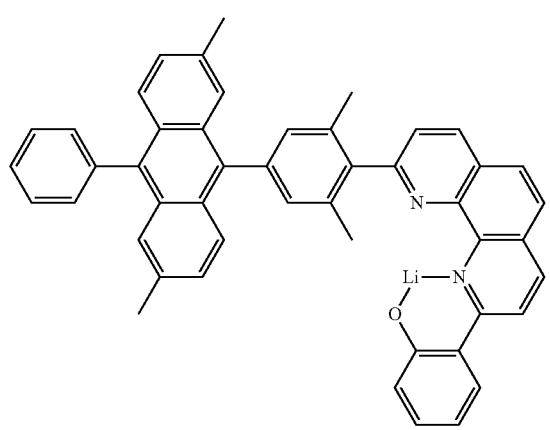
C33
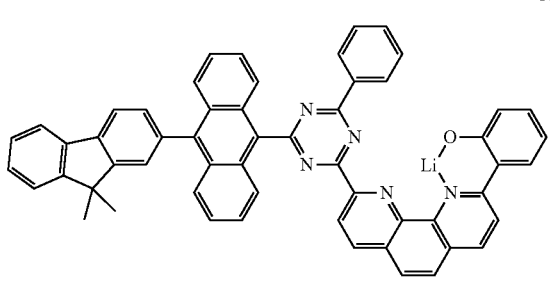
C34
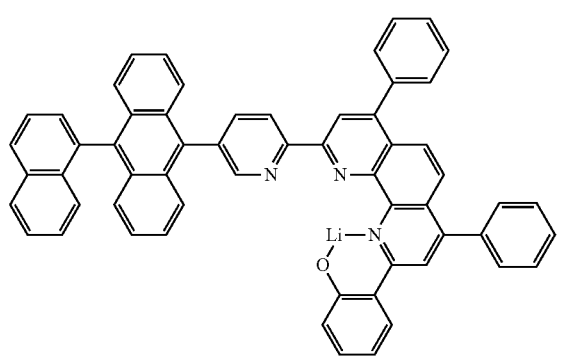
C35
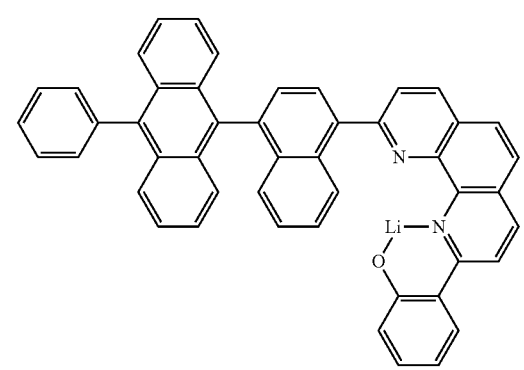
C36
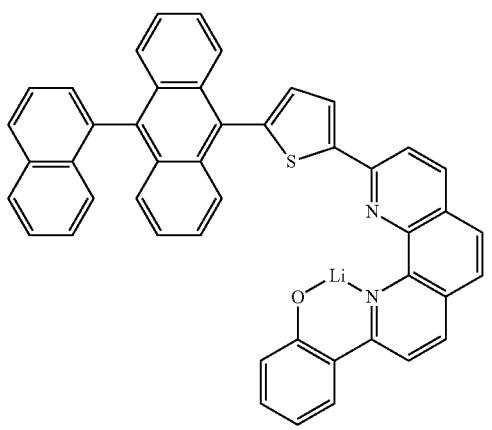
C37
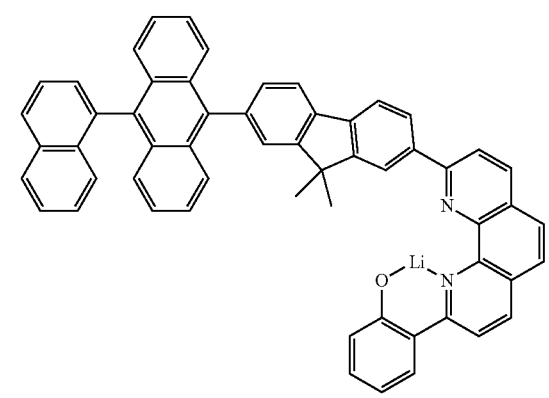

C38
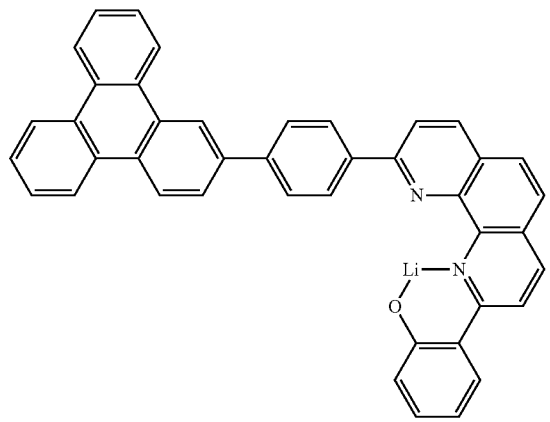
C41
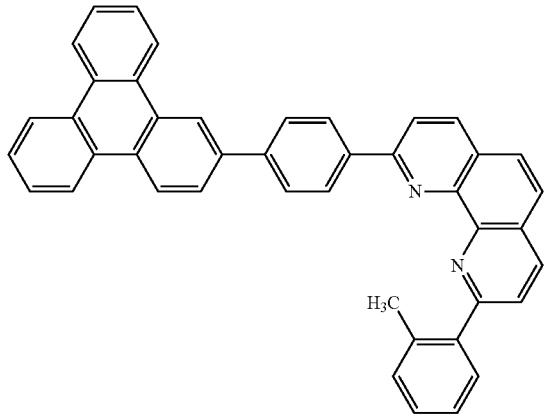
C39
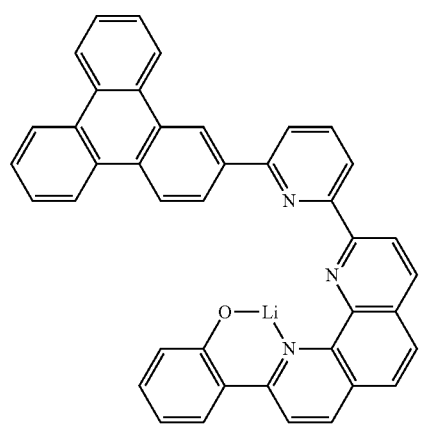
C42
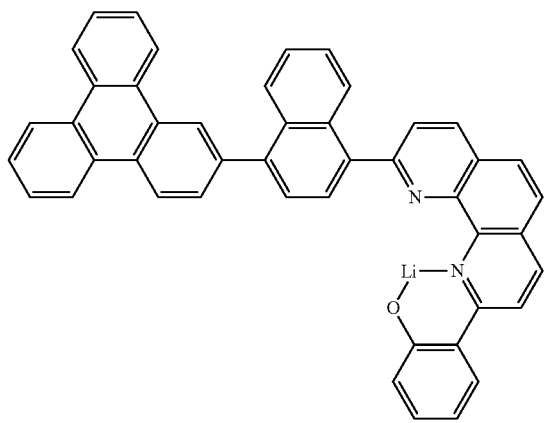
C40
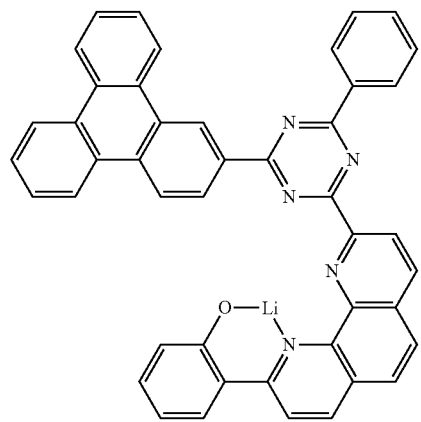
C43
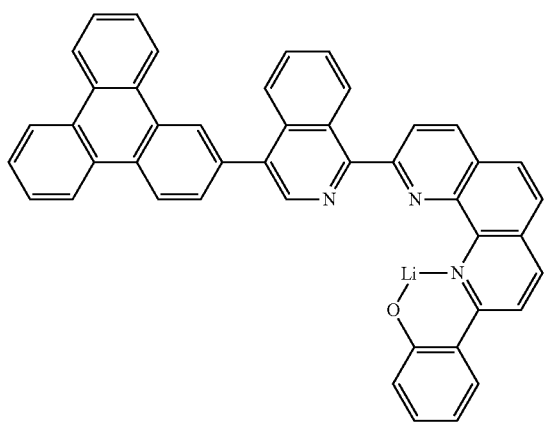

C44
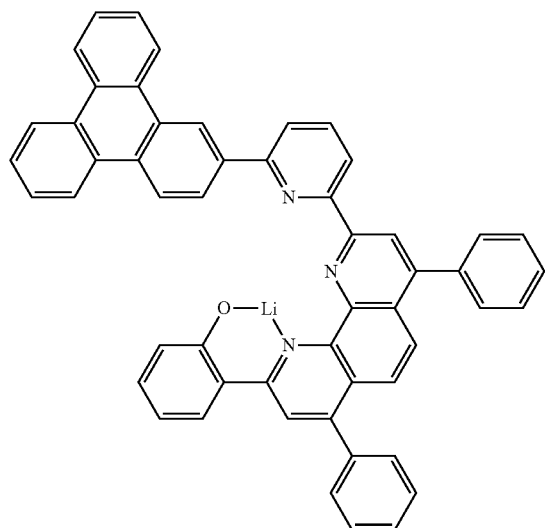
C45
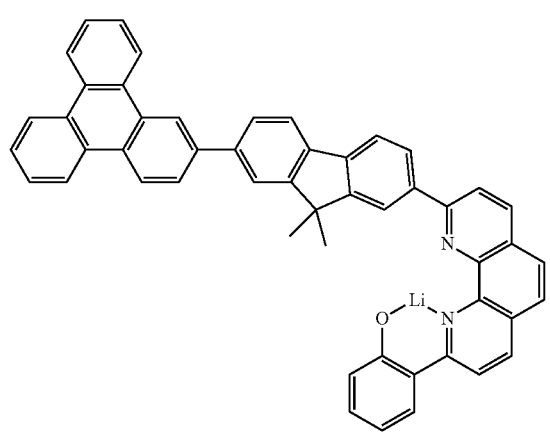
C46
C47
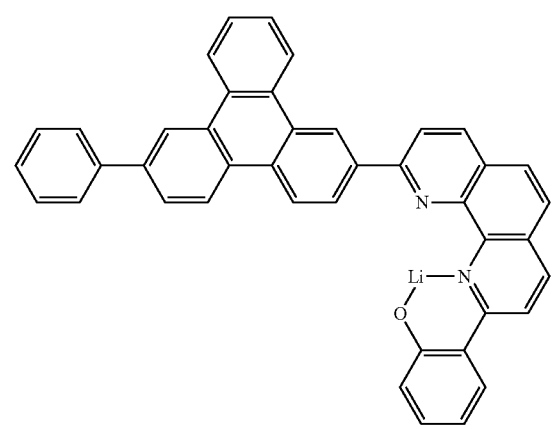
C48
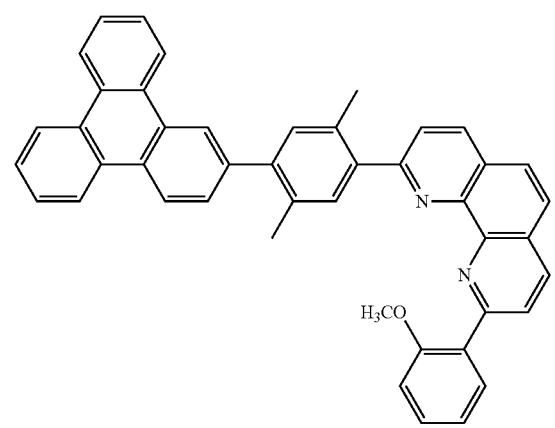
C49
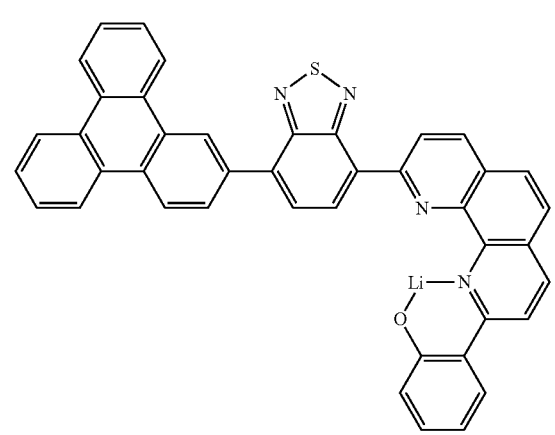

C50

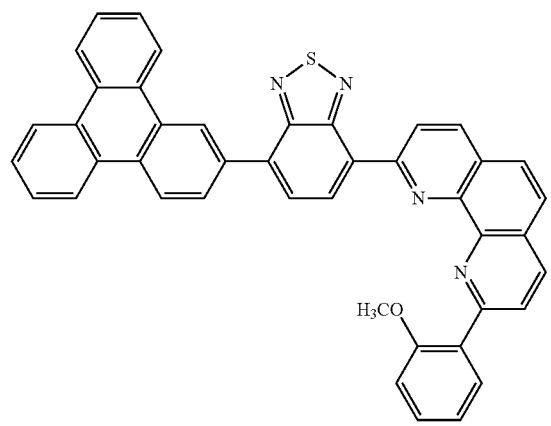

6. An organic electroluminescence device comprising a pair of electrodes consisting of a cathode and an anode, and between the pairs of electrodes comprising at least a light emitting layer, one or more layers of organic thin film layers, wherein at least one of the at least a light emitting layer and the one or more organic thin film layers comprises the phenanthroline-based compound with a general formula (1) according to claim 1.

7. The organic electroluminescence device according to claim 6, wherein the at least a light emitting layer comprises the phenanthroline-based compound with a general formula (1) used as a phosphorescent host material.

8. The organic electroluminescence device according to claim 6, wherein the at least a light emitting layer comprises the phenanthroline-based compound with a general formula (1) used as a thermally activated delayed fluorescence host material.

9. The organic electroluminescence device according to claim 6, wherein the at least a light emitting layer comprises the phenanthroline-based compound with a general formula (1) used as a thermally activated delayed fluorescence dopant material.

10. The organic electroluminescence device according to claim 6, wherein the at least a light emitting layer comprises a phosphorescent dopant material.

11. The organic electroluminescent device according to claim 10, wherein the phosphorescent dopant material is an iridium complex.

12. The organic electroluminescence device according to claim 6, wherein the one or more organic thin film layers comprises the phenanthroline-based compound with a general formula (1) used as an electron transporting material.

13. The organic electroluminescence device according to claim 6, wherein the one or more organic thin film layers comprises the phenanthroline-based compound with a general formula (1) used as a hole blocking material.

14. The organic electroluminescent device according to claim 6, wherein the at least a light emitting layer comprises one of the compounds as the following formulas:

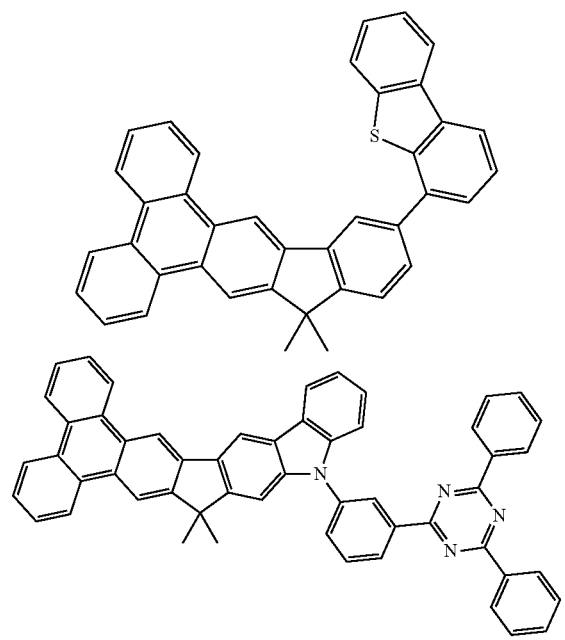

15. The organic electroluminescent device according to claim 6, wherein the one or more organic thin film layers are one or more electron transporting layers or one or more hole blocking layers, and at least one of the one or more electron transporting layers and the one or more hole blocking layers comprises one of the compounds as the following formulas:

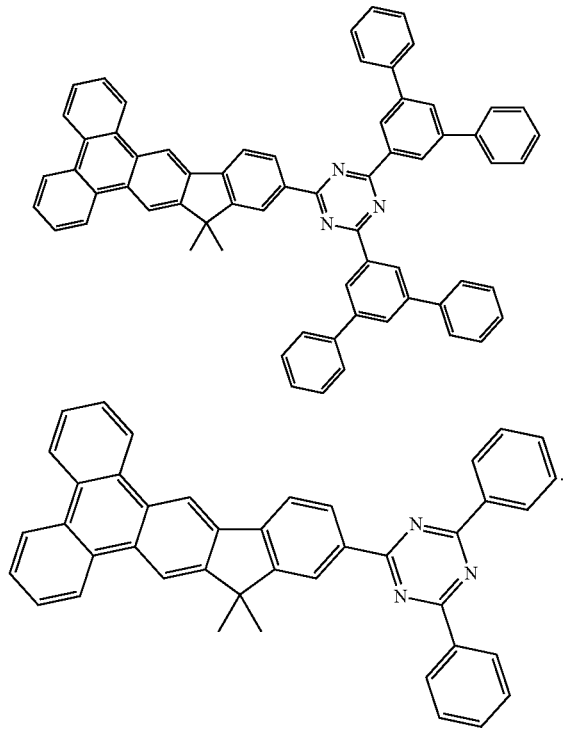

16. The organic electroluminescence device according to claim 15, wherein the one or more electron transporting layer comprises lithium or 8-hydroxy-quinolinolato-lithium.

17. The organic electroluminescence device according to claim 6, wherein the at least a light emitting layer emits phosphorescent light selected from the group consisting of red, blue, green and yellow lights.

18. The organic electroluminescence device according to claim 6, wherein the at least a light emitting layer emits thermally activated delayed fluorescent light selected from the group consisting of red, blue, green and yellow lights.

19. The organic electroluminescence device according to claim 6, wherein the device is an organic light emitting device.

20. The organic electroluminescent device according to claim 6, wherein the device is a lighting panel.

21. The organic electroluminescent device according to claim 6, wherein the device is a backlight panel.

\* \* \* \* \*